US012582632B2

(12) United States Patent
Maccecchini

(10) Patent No.: US 12,582,632 B2
(45) Date of Patent: Mar. 24, 2026

(54) INHIBITION OF NEUROLOGICAL INJURIES DUE TO INFECTIONS VIA ADMINISTRATION OF BUTANETAP AND ANALOGS THEREOF

(71) Applicant: ANNOVIS BIO, INC., Berwyn, PA (US)

(72) Inventor: Maria Maccecchini, West Chester, PA (US)

(73) Assignee: ANNOVIS BIO, INC., Berwyn, PA (US)

( * ) Notice: Subject to any disclaimer, the term of this patent is extended or adjusted under 35 U.S.C. 154(b) by 609 days.

(21) Appl. No.: 17/746,678

(22) Filed: May 17, 2022

(65) Prior Publication Data

US 2022/0370412 A1 Nov. 24, 2022

Related U.S. Application Data

(60) Provisional application No. 63/189,912, filed on May 18, 2021.

(51) Int. Cl.

| | |
|---|---|
| ***A61K 31/407*** | (2006.01) |
| ***A61P 25/28*** | (2006.01) |
| *A61K 9/00* | (2006.01) |

(52) U.S. Cl.

CPC ............ *A61K 31/407* (2013.01); *A61P 25/28* (2018.01); *A61K 9/0053* (2013.01)

(58) Field of Classification Search

None

See application file for complete search history.

(56) References Cited

U.S. PATENT DOCUMENTS

| | | | |
|---|---|---|---|
| 5,171,750 | A | 12/1992 | Brossi et al. |
| 5,409,948 | A | 4/1995 | Greig et al. |
| 6,410,747 | B1 | 6/2002 | Greig et al. |
| 6,495,700 | B1 | 12/2002 | Bruening et al. |
| 6,683,105 | B2 | 1/2004 | Greig et al. |
| 7,153,882 | B2 | 12/2006 | Grieg et al. |
| 7,625,942 | B2 | 12/2009 | Bruinsma et al. |
| 7,786,162 | B2 | 8/2010 | Grieg et al. |
| 7,994,210 | B2 | 8/2011 | Bruinsma et al. |
| 8,258,172 | B2 | 9/2012 | Greig et al. |
| 8,691,864 | B2 | 4/2014 | Greig et al. |
| 2002/0094999 | A1 | 7/2002 | Grieg et al. |
| 2005/0013869 | A1 | 1/2005 | Chaw et al. |
| 2005/0182044 | A1 | 8/2005 | Bruinsma |
| 2005/0272804 | A1 | 12/2005 | Bruinsma |
| 2007/0037848 | A1 | 2/2007 | Masters et al. |
| 2010/0298389 | A1 | 11/2010 | Elmaleh et al. |
| 2011/0021594 | A1 | 1/2011 | Grieg et al. |
| 2018/0338950 | A1 | 11/2018 | Maccecchini |
| 2019/0381007 | A1 | 12/2019 | Maccecchini |

FOREIGN PATENT DOCUMENTS

| | | |
|---|---|---|
| WO | WO0166114 | 9/2001 |
| WO | WO0248150 | 6/2002 |
| WO | WO03082270 | 10/2003 |
| WO | WO2004034963 | 4/2004 |
| WO | WO2005089746 | 9/2005 |
| WO | WO2005123068 | 12/2005 |
| WO | WO2010117727 | 10/2010 |
| WO | WO2012154285 | 11/2012 |
| WO | WO2014/179303 A1 | 11/2014 |

OTHER PUBLICATIONS

Maccecchini et al. "Posiphen lowers amyloid precursor protein and amyloid beta as well as acetylcholinesterase levels in culture, animals and humans" International Conference on Alzheimer's Disease; Jul. 12, 2009 (Abstract is retrieved from http://www.qrpharma.com/pdf/ICAD_Posiphen_06-30-2009.pdf on May 19, 2012; Publication date is retrieved from http://www/grpharma.com/pdf/WCBR_Posiphen_01/206/20099%20Poster.pdf on May 19, 2012) abstract, Figs. 1, 3, 4, 8(2).

Shaw et al., "Phenserine regulates translation of B-amyloid precursor protein mRNA by a putative interleukin-1 responsive element, a target for drug development" PNAS, vol. 98, No. 13; pp. 7605-7610, (Jun. 19, 2001).

Galvan, et al., "Reversal of Alzheimer's-like pathology and behavior in human APP transgenic mice by mutation of Asp664," PNAS, May 2, 2006, 103(18): pp. 7130-7135.

Cullen et al. "Brain Beta-Amyloid 42 in Mice Treated Orally with Posiphen Tartrate is Significantly Lower than in Vehicle Controls," 9th International Geneva/Springfield Symposium on Advances in Alzheimer Therapy; (Apr. 19, 2006).

Holloway et al. "Mechanism of Action of Posiphen in CSF of mildly Cognitive Impaired Patients," QR Pharma, Inc., Radnor, PA.

Soares et al., "Aβ Variability and Effects of Gamma Secretase Inhibition on Plasma and Cerebrospinal Fluid Levels of Aβ Peptide in Healthy Volunteers" Pfizer Global Research and Development, New London, CT.

Marutle et al. "Modulation of human neural stem cell differentiation in Alzheimer (APP23) transgenic mice by phenserine" The National Academy of Sciences of the USA; vol. 104, No. 30, pp. 12506-12511, (Jul. 24, 2007).

Brazzolotto et al., "Structural Changes Associated with Switching Activities of Human Iron Regulatory Protein 1*" The Journal of Biological Chemistry; vol. 277, No. 14, pp. 11995-12000, (2002).

(Continued)

*Primary Examiner* — Po-Chih Chen

(74) *Attorney, Agent, or Firm* — Davidson Kappel LLC

(57) ABSTRACT

The invention relates to methods of inhibiting or treating neurological damage in a human who is infected by or at risk of infection by a virus, a bacterium, a fungus, a protozoan or a parasite that can cause neurological damage, comprising administering to a human a compound selected from the group consisting of Formula (I), Formula (II), Formula (III) or Formula (IV) or pharmaceutically acceptable salts thereof.

16 Claims, 9 Drawing Sheets

(56) References Cited

OTHER PUBLICATIONS

Shaw et al., "Phenserine regulates translation of β-amyloid precursor protein mRNA by a putative interleukin-1 responsive element, a target for drug development" PNAS, vol. 98, No. 13; pp. 7605-7610, (Jun. 19, 2001).
Lahiri et al. "The Experimental Alzheimer's Disease Drug Posiphen [(+)-Phenserine] Lowers Amyloid-β Peptide Levels in Cell Culture and Mice" The Journal of Pharmacology and Experimental Therapeutics, vol. 320, No. 1; pp. 386-396; (2007).
Selkoe, "Defining Molecular Targets to Prevent Alzheimer Disease" American Medical Association; pp. 192-195; (2005).
Kadir et al. "Effect of Phenserine Treatment on Brain Functional Activity and Amyloid in Alzheimer's Disease" American Neurological Association, Wiley-Liss, Inc.; pp. 621-631; (2008).
Khachaturian, "Diagnosis of Alzheimer's Disease" Arch Neurology; vol. 42, pp. 1097; (Nov. 1985).
Cahill et al. "Amyloid Precursor Protein and Alpha Synuclein Translation, Implications for Iron and Inflammation in Neurodegenerative diseases" *Biochim Biophys Acta.* 1790(7): 615-628 (Jul. 2009).
Maccecchini et al. "Posiphen as a candidate drug to lower CSF amyloid precursor protein, amyloid-β peptide and τ levels: target engagement, tolerability and pharmacokinetics in humans" J Neurol Neurosurg Psychiatry; vol. 83; pp. 894-902; (2012).
Duce et al. "Iron-Export Ferroxidase Activity of β-Amyloid Precursor Protein Is Inhibited by Zinc in Alzheimer's Disease" Cell; pp. 1-10; (2010), doi: 10.1016/j.cell.2010.08.014.
Kounnas et al. "Modulation of x-Secretase Reduces β-Amyloid Deposition in a Transgenic Mouse Model of Alzheimer's Disease" Neuron; pp. 1-12; (2010).
Mikkilineni et al. "The Anticholinesterase Phenserine and Its Enantiomer Posiphen as 5' Untranslated-Region-Directed Translation Blockers of the Parkinson's Alpha Synuclein Expression" Hindawi Publishing Corporation; vol. 2012, Article ID 142372.
Venti et al. "The Integrated Role of Desferrioxamine and Phenserine Targeted to an Iron-Responsive Element in the APP-mRNA 5'-Untranslated Region" Ann. N.Y. Acad. Sci. vol. 1035: pp. 34-58 (2004).
Bandyopadhyay et al. "Novel 5' Untranslated Region Directed Blockers of Iron-Regulatory Protein-1 Dependent Amyloid Precursor Protein Translation: Implications for Down Syndrome and Alzheimer's Disease" PLOS One; vol. 8, Issue 7; pp. 1-14 (2013).
Maccecchini, "Targeting Alzheimer's with Novel Therapeutics" QR Pharma, Inc. Neuroscience Network; presented by Maria Maccecchini on May 11, 2010.
Harold W Holloway et al: "Posiphen and Analogs: Experimental Alzheimer' Agents that Reduce Amyloid-[beta] Peptide by Lowering Amyloid Precursor Protein Levels in Culture and In Vivo" , 42nd Annual Winter Conference on Brain Research , Jan. 25, 2009 (Jan. 25, 2009) , 42nd Annual Winter Conference on Brain Research. Abstract only.
Maccecchini et al: "Targeting Alzheimer's with Novel Therapeutics", May 11, 2010 (May 11, 2010), Neuroscience Network, <<http://www.qrpharma.comlpdf/2010-5-11 Alzheimers Research Today Maria Maccecchinislides.pdf>>. Last accessed Jul. 22, 2014.
Maria L. Maccecchini: "Mechanism of Action of Posiphen : From Model to Human" , Jan. 26, 2011 (Jan. 26, 2011) , 44nd Annual Winter Conference on Brain Research, <<http://wwwqrpharma.com/pdfIWCBR Talk Jan. 2011.pdf>>. Last accessed Jul. 22, 2014.
Kadir et al: "Long-term effect of phenserine treatment in Alzheimer patients as assessed by PET and CSF biomarkers", Alzheimer's & Dementia the Journal of the Alzheimer's Association vol. 5, No. 4; p. 6.
Melo et al. "Prion Protein Aggregation and Neurotoxicity in Cortical Neurons", Annals of the NY Academy of Sci., 1096, 1, 2007.
Maccecchini et al. (Poster presentations, Alzheimer's and Dementia, Jul. 2009, 5, 4, S1, p. 247-248).
Lahiri et al. (The J of Pharmacology and Experimental Therapeutics, 320, 1, 386-396, 2007).
Tomiyama et al., (The J of Biol. Chem, 271, 12, 6839-44, 1996).
Galvan, et al., "Reversal of Alzheimer's-like pathology and behavior in human APP transgenic mice by mutation of Asp664," PNAS, May 2, 2006, I03(18): pp. 7130-7135.
Nikolaev, et al., "APP binds DR6 to trigger axon pruning and neuron death via distinct caspases," Nature, Feb. 19, 2009, 457(19): pp. 981-990.
Takeda, et al., "Mechanisms ofNeuronal Death in Synucleinopathy," Journal ofBiomedicine and Biotechnology, 2006, vol. 2006, Article ID 19365, pp. 1-4.
Rogers, et al., "The alpha-synuclein 5 'untranslated region targeted translation blockers: anti-alpha synuclein efficacy of cardiac glycosides and Posiphen," .1. Neural Transm, Oct. 15, 2010, DOI 10.1007/s00702-010-0513-5.
Cho, et al., "Selective Translational Control of the Alzheimer Amyloid Precursor Protein Transcript by Iron Regulatory Protein-1," Journal ofBiological Chemistry, Oct. 8, 2010, 285(41): pp. 31217-31232.
Khachaturian, "Diagnosis of Alzheimer's Disease," Arch Neural, Nov. 1985, 42: pp. 1097-1105.
International Search Report from International WIPO Publication No. WO 2012/154285 dated Aug. 17, 2012.
Maccecchini et al. "Posiphen lowers amyloid precursor protein and amyloid beta as well as acetylcholinesterase levels in culture, animals and humans" International Conference on Alzheimer's Disease; Jul. 12, 2009 (Abstract is retrieved from http://www.qrpharma.com/pdf/ICAD_Posiphen_06-30-2009.pdf on May 19, 2012; Publication date is retrieved from http://www/grpharma.com/pdf/WCBR_Posiphen_01%206%2009%20Poster.pdf on May 19, 2012) abstract, Figs. 1, 3, 4, 8(2).
Greig et al. "The experimental Alzheimer drug phenserine: preclinical pharmacokinetics and pharmacodynamics" Acta Neurol Scand 2000: Supplement 176: pp. 74-84.
Office Action from corresponding Korean Patent Application No. 10-2013-7025992 dated Jul. 30, 2018.
Janas et al. "The cholinesterase inhibitor, phenserine, improves Morris water maze performance of scopolamine-treated rats" Life Sciences, Pergamon Press, Oxford, GB, vol. 76, No. 10, (Jan. 21, 2005) pp. 1073-1081.
Pike et al. "Effect of tetrahydroaminoacridine, a cholinesterase inhibitor, on cognitive performance following experimental brain injury" Journal of Neurotrauma, vol. 14, No. 12, (Dec. 1997) pp. 897-905.
David et al. "Cognitive impairments Induced by Concussive Mild Traumatic Brain Injury in Mouse Are Ameliorated by Treatment with Phenserine via Multiple Non-Cholinergic and Cholinergic Mechanisms" POLS One, vol. 11, No. 6, (Jun. 2, 2016) pp. e0156493.
International Search Report from International PCT Application No. PCT/US2016/046794 dated Feb. 23, 2017.
Greig et al., "An Overview of Phenserine Tartrate, A Novel Acetylcholinesterase Inhibitor for the Treatment of Alzheimer's Disease" Current Alzheimer Research, Bentham Science Publishers Ltd., vol. 2, pp. 281-290 (2005).
Jacobson et al., "Investigational drugs for the treatment of AD: what can we learn from negative trials?" *Alzheimer's Research & Therapy*, BioMed Central Ltd., vol. 3; No. 14; pp. 1-8 (2011).
U.S Department of Health and Human Services Food and Drug Administration Center for Drug Evaluation and Research (CDER) "Guidance for Industry Estimating the Maximum Safe Starting Dose in Initial Clinical Trials for Therapeutics in Adult Healthy Volunteers"; Jul. 6, 2005.
Maccecchini et al. "Posiphen: Experimental Alzheimer Agent that Lowers Amyloid Precursor Protein Levels in Culture and In Vivo"; Dept. Psychiatry, Institute Psychiatric Research, Indiana Univ., Indianapolis, IN: Department of Neuroscience, Center of Aging, Medical University of S. Carolina, Charleston, SC;. PowerPoint Presentation Dated Jan. 2011, (abstract only).
Summons to Attend Oral Proceedings mailed on Apr. 25, 2019 in connection to European Patent Application No. 12 782 326.8.
Novak et al. (Huntington's Disease, BMJ, Jul. 3, 2010). (Year: 2010).
Larson et al. (Annu. Rev. Publ. Health 13L431-49) (Year: 1992).

(56) References Cited

OTHER PUBLICATIONS

CAS Registry (1998, p. 1) (Year: 1998), CAS Registry No. 116839-68-0.
Phukan et al. (http://neurology.thelancet.com, vol. 6, Nov. 2007). (Year: 2007).
Klein (Phenserine, Expert Opin Investig. Drugs 2007, 16(7): 1087-1097 (Year: 2007).
Enright (https://louisaenright.com/2011 /11 /), 2011 (Year: 2011).
Anna M. Lija et al. "Neurotrophic and Neuroprotective Actions of (−) − and (+)-Phenserine, Candidate Drugs for Alzheimer's Disease" PLOS one; Jan. 2013, vol. 8, Issue 1.
Hien T. Tran et al. (Controlled cortical impact traumatic brain injury in 3xTg-AD mice causes acute intra-axonal amyloid-[3 accumulation and independently accelerates the development of tau abnormalities. J Neurosci. Jun. 29, 2011;31 (26) :9513-25. doi:10.1523/JNEUROSCI.0858-11.2011. PMID: 21715).
Victoria Johnson et al. (Nat Rev Neurosci. May 2010; 11 (5): 361-370).
Yazhour Li et al. "Liraglutide is neurotrophic and neuroprotective in neuronal cultures and mitigates mild traumatic brain injury in mice" Journal of Neurochemistry; International Society for Neurochemistry, J. Neurochem (2015) 135, 1203-1217.
European Search Report from corresponding application EP 18 80 5102 dated May 12, 2021.
Ashley I. Bush, "The Metal Theory of Alzheimer's Disease", Journal of Alzheimer's Disease 33 (2013) S277-S281.
Qin et al., "Herpesviral infections and antimicrobial protection for Alzheimer's disease: Implications for prevention and treatment", Journal of Medical Virology, 2019, pp. 1-10. Abstract; p. 4, col. 2, para 3; p. 5, para 3.
Bandyopadhyay et al., "Alzheimer's disease therapeutics targeted to the control of amyloid precursor protein translation: Maintenance of brain iron homeostatis", Biochemical Pharmacology, 2014, vol. 88, pp. 486-494.
International Search Report issued on Aug. 29, 2022, from corresponding International Application No. PCT/US22/29656.
Written Opinion of the International Searching Authority issued on Aug. 29, 2022, from corresponding International Application No. PCT/US22/29656.

| Marker | (%) Drop | p-values |
|---|---|---|
| APP | 39.8 | 0.0080 |
| CTFβ | 46.8 | 0.0024 |
| CTFα | 48.5 | 0.0031 |
| Aβ42 | 67.9 | 0.0008 |
| Aβ40 | 13.7 | 0.1627 |
| GAPDH | 11.4 | 0.8425 |
| Synaptophysin | 6.3 | 0.9619 |

| Human Biomarker | CSF % of Time 0 | p-Value |
|---|---|---|
| **sAPP α** | -59.9% | 0.0006 |
| **sAPP β** | -57.7% | 0.0001 |
| **Aβ42** | -51.4% | 0.0533 |
| **Tau** | -46.2% | 0.0020 |
| **p-Tau** | -61.0% | 0.0005 |
| **aSYN** | -41.2% | 0.0912 |

INHIBITION OF NEUROLOGICAL INJURIES DUE TO INFECTIONS VIA ADMINISTRATION OF BUTANETAP AND ANALOGS THEREOF

FIELD OF THE INVENTION

The present patent application concerns a method of inhibiting, preventing or treating neurological injuries due to viral, bacterial, fungal, protozoan, or parasitic infections in humans and in animals via administration of Butanetap (Posiphen) or related compounds.

BACKGROUND OF THE INVENTION

Infections of the Brain

A brain infection is a bacterial, viral, fungal, protozoan or parasitic infection of the tissue of the brain itself or the membranes surrounding the brain and spinal cord. Bacteria and viruses are the most common causes of brain infections.

Infections are one of the major causes interfering with healthy aging. Historically speaking, when we increased the lifespan from 35 to 50, it was by covering the sewers. When we increased the lifespan from 50 to 75, it was with the use of antibiotics. Now we are looking for viruses in all of the major life-threatening diseases of our time—Alzheimer's, Parkinson's, cancer—and in fact it turns out to be a major component of all of them (Robin Seaton Jefferson, Forbes, Jul. 25, 2018 Evidence Mounts That Germs May Cause Alzheimer's).

Novel research approaches are studying and mapping the microbial population of microorganisms, some helpful and some pathological, that exists inside the brain-utilizing autopsied brain samples that tested positive for Alzheimer's disease pathology. The brain microbiome project found that microbes are indeed at the heart of Alzheimer's disease. Bacteria and viruses definitely associated with the development of Alzheimer's disease to date are herpes, HIV, lime disease, gum disease, other microbes are being studied.

Since 2010, research has shown that (Hongmei et al. Translational Neurodegeneration volume 7, Article number: 34 (2018) Amyloid, tau, pathogen infection and antimicrobial protection in Alzheimer's disease—conformist, nonconformist, and realistic prospects for AD pathogenesis):

- For unknown reasons in a "sick" brain, the levels of iron is high and the synthesis of abeta and other neurotoxic aggregating proteins are upregulated, leading to overproduction of iron in the sick brain. When a nerve cell becomes injured, iron flows into the cell. High iron levels increase the translation of neurotoxic proteins, leading to impairment of axonal transport, inflammation, and nerve cell death.
- Neurons use amyloid beta to kill or trap (clump around) microbes to protect the brain. But in doing so, in Alzheimer's patients, the process creates a buildup of amyloid plaques.
- These plaques trigger the production of tangles—clumps of another brain protein called tau—in the brain, which then go on to cause chronic inflammation and eventually Alzheimer's disease.

Therefore, a viral, bacterial, fungal protozoan, or parasitic infection of the brain leads to amyloid beta and tau being over-produced and the plaques and tangles are trapping the virus to protect the brain cells from infection. However, overproduction of these proteins leads to the toxic cascade causing nerve cell death and therefore leads to Alzheimer's disease or other neurodegenerative diseases.

While infections do not necessarily cause neurodegeneration, the fact that these proteins are overexpressed could lead to neurodegeneration years later. The viruses and bacteria studied are the tip of the iceberg—there are dozens of microbes, and they can all have negative effects on the brain. Thus, a need exists to identify methods to treat and prevent neurodegeneration resulting from the overexpression of proteins that occurs during microbial infections (e.g., viral, bacterial, fungal, etc.)

SUMMARY OF THE INVENTION

It is an object of the invention to provide a method to inhibit, prevent or treat neurological damage (e.g., neurodegeneration) and neurological conditions or diseases in mammals such as humans who are at risk of or infected by a virus, a bacterium, a fungus, a protozoan or a parasite that can cause neurological damage.

In accordance with the above objects and others, the invention is directed in part to a method to inhibit, prevent or treat neurological damage (e.g., neurodegeneration) and neurological conditions or diseases in mammals (e.g., humans) who are infected by or at risk of infection by a virus, bacterium, fungus, protozoan or parasite that can cause neurological damage (e.g., a neurological disease or a neurodegenerative disease) comprising, or consisting of, administering to the human a therapeutically effective amount of butanetap, active metabolites of butanetap, therapeutically effective analogues of butanetap, compounds that are similar to butanetap as described herein, pharmaceutically acceptable salts and complexes thereof, together with one or more pharmaceutically acceptable excipients. In certain embodiments, butanetap is administered orally in an amount from about 1 mg to about 120 mg, preferably on a once-a-day basis. In certain preferred embodiments, butanetap is administered in an amount from about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, and numbers in between these numbers, and all further integers to about 120 mg, preferably on a once a day basis. In certain preferred embodiments, butanetap is administered orally in a dose from about, e.g., 2 mg to about 80 mg. In other embodiments, the butanetap dose is administered intravenously in an amount from about 0.1 to about 25 mg/day. In other preferred embodiments, the butanetap dose is administered intraperitoneally/intramuscularly (IP/IM) in a dose from about 0.3 to about 70 mg/day. In certain embodiments, the treatment of the present invention is initiated to human(s) who has been infected by a virus, bacterium, fungus, protozoan or parasite that can cause neurological damage, prior to the infection directly or indirectly causing a neurological disorder or neurological damage (e.g., a neurodegenerative disease).

In certain embodiments, the invention is directed to maintaining (heavy) metal homeostasis in a human(s) who is at risk of exposure to infection by or is infected by a virus, bacterium, fungus, protozoan or parasite that can cause neurological damage, and thereby inhibiting or preventing neurological damage in the human by maintaining (heavy) metal homeostasis in the human(s) in accordance with the treatment (administration of butanetap) as set forth in this paragraph, the previous paragraph and herein in general. In certain embodiments, the treatment of the present invention is initiated to human(s) who has been infected by a virus, bacterium, fungus, protozoan or parasite that can cause neurological damage, prior to the infection directly or indirectly causing a neurological disorder or neurological damage (e.g., a neurodegenerative disease).

In certain embodiments of each of the methods described above, the oral pharmaceutical composition includes from about 1 mg to about 120 mg butanetap or a pharmaceutically acceptable salt thereof, the IP/IM pharmaceutical composition includes from about 0.3 to about 70 mg butanetap or a pharmaceutically acceptable salt thereof, and the intravenous (IV) pharmaceutical formulation includes from about 0.1 to about 25 mg butanetap or a pharmaceutically acceptable salt thereof. Between about 120 mg/day and 200 mg/day, butanetap turns toxic. The dose of 1 nM B butanetap was found to be efficacious, as was the (extrapolated) plasma level of about 10 to about 10,000 nM in tissue culture.

In certain preferred embodiments of the methods described herein, peak plasma circulating levels of butanetap in humans range, e.g., from about 1 ng/mL to about 380 ng/mL, in certain embodiments from about 2 ng/mL to about 20 ng/mL, and more preferably from about 3.7 ng/mL to about 120 ng/mL. In certain preferred embodiments, the peak plasma circulating level is reached within about 2 hours after administration of butanetap to humans. In certain embodiments, the peak plasma circulating level is reached within about 3 hours after administration of butanetap to the humans. In certain embodiments, the plasma circulating level of butanetap is equal to or greater than about 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 mg/mL, 15 ng/mL, 16 ng/mL, 17 ng/mL, 18 ng/mL, 19 ng/mL, or 20 ng/mL for at least 9 hours, and preferably for at least 12 hours, after administration of butanetap to humans. In certain embodiments, the steady-state plasma concentration of butanetap is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 11, 112, 113, 114, 115, 116, 117, 118, 119 or 120 ng/mL. In certain embodiments, the half-life of butanetap in cerebrospinal fluid after administering is about 12 hours, and the half-life of butanetap in plasma after administering is about 5 hours. In certain embodiments, the administration of butanetap to humans results in a brain level of butanetap that range from about 4 to about 10 times the plasma level of butanetap in those patients. In certain embodiments, the concentration of butanetap in the brain of humans is from about 8 ng/g to about 3040 ng/g, in certain embodiments from about 30 ng/g to about 960 ng/g.

With respect to each of the methods described above, butanetap, a pharmaceutically acceptable salt thereof, analogues or similar compounds as described herein may be administered, e.g., orally, parenterally, sublingually, via suppository, nasally, topically, transdermally, or via implant under the skin.

The invention is further directed in part to a method for inhibiting or treating neurological damage in a mammal (e.g., human) who is infected by a virus, bacterium, fungus, protozoan or parasite that can cause neurological damage; or a method for inhibiting or treating neurological damage in a healthy human who is at risk of exposure to infection by a virus or bacteria that can cause neurological damage (e.g., a neurological disease or a neurodegenerative disease), comprising administering to the human a compound selected from the group consisting of Formula (I), Formula (II), Formula (III) and Formula (IV):

(I)

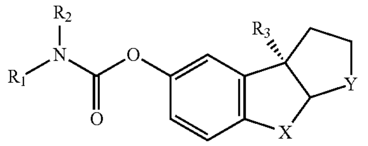

or (II)

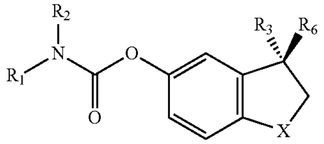

(III)

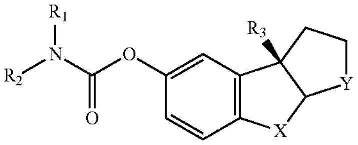

In Formula (I) and Formula (II), $R_1$ and $R_2$ are, independently, hydrogen, branched or straight chain $C_1$-$C_8$ alkyl, substituted or unsubstituted aryl, heteroaryl, or aralkyl; $R_3$ is branched or straight chain $C_1$-$C_4$ alkyl or heteroalkyl or $C_4$-$C_8$ alkyl or heteroalkyl, or substituted or unsubstituted aryl; X and Y are, independently, O, S, alkyl, hydrocarbon moiety, $C(H)R_4$, or $NR_5$, wherein $R_4$ and $R_5$ are, independently, hydrogen, oxygen, branched or straight chain $C_1$-$C_8$ alkyl, $C_2$-$C_8$ alkenyl or $C_2$-$C_8$ alkynyl, aralkyl, or substituted or unsubstituted aryl; and $R_6$ is hydrogen, $C_1$-$C_8$ alkyl, $C_1$-$C_8$ alkenyl, $C_2$-$C_8$ alkynyl, aralkyl, or substituted or unsubstituted aryl, or $(CH_2)_nR_7$, where $R_7$ is hydroxy, alkoxy, cyano, ester, carboxylic acid, substituted or unsubstituted amino, and n is from 1 to 4.

In certain embodiments, the compound of Formula (I) and Formula (II) is the substantially pure (+)-enantiomer.

In certain embodiments, the compound of Formula (I) is butanetap or its active metabolites.

In preferred embodiments, the compound is butanetap of Formula IV as follows:

(IV)

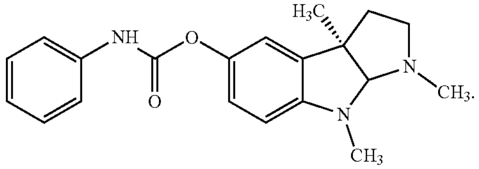

In Formula (III), $R_1$ and $R_2$ are, independently, hydrogen, branched or straight chain $C_1$-$C_8$ alkyl, substituted or unsubstituted aryl, heteroaryl, or aralkyl; $R_3$ is branched or straight chain $C_1$-$C_4$alkyl or heteroalkyl or $C_4$-$C_8$ alkyl or heteroalkyl, or substituted or unsubstituted aryl; X is $NR_5$, wherein $R_5$ is $C_{2-8}$ alkenyl, $C_{2-8}$ alkynyl, or aralkyl, and Y is selected from $C(H)R_4$ or $NR_5$, wherein $R_4$ and $R_5$ are, independently, hydrogen, branched or straight chain $C_{1-8}$ alkyl or heteroalkyl, alkenyl, or $C_2$-$C_8$ alkynyl, aralkyl.

The compound is administered via a route selected from the group consisting of orally, parenterally, sublingually, via suppository, nasally, topically, transdermally, and via implant under the skin. In certain embodiments, the compound is administered to the human until the human is no longer infected with the viral or bacterial infection. In certain embodiments, the compound is administered to the human until the human is no longer infected with the viral or bacterial infection and neurological damage in the human has been treated. In certain embodiments, the compound is administered chronically to treat the neurological damage in the human.

In certain preferred embodiments, the compound is butanetap and the butanetap is administered in an amount as set forth in this disclosure.

In certain embodiments, the invention is also directed to a method of maintaining heavy metal homeostasis or restoring heavy metal homeostasis in a human who is infected by or at risk of being infected by a virus or a bacteria that can cause neurological damage to the human, comprising administering to the human a compound selected from the group consisting of Formula (I), Formula (II), Formula (III) and Formula (IV) as set forth in this paragraph and as described in the following paragraphs.

In certain embodiments, the treatment of the present invention is initiated to human(s) who has been infected by a virus, bacterium, fungus, protozoan or parasite that can cause neurological damage, prior to the infection directly or indirectly causing a neurological disorder or neurological damage (e.g., a neurodegenerative disease).

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in biochemistry, analytical chemistry and organic chemistry are those well-known and commonly employed in the art. Standard techniques or modifications thereof are used for chemical syntheses and chemical analyses.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

As used herein, the terms "butanetap" and "posiphen" are used interchangeably to refer to (3aR)-1,3a,8-trimethyl-1,2,3,3a,8,8a-hexahydropyrrolo[2,3-b]indol-5-yl phenylcarbamate or a salt thereof.

As used herein, the term "APP" refers to amyloid precursor protein.

As used herein, the term "Aβ" refers to amyloid-β peptide.

As used herein, the term "Tau" refers to any of the products of alternative splicing from the gene designated MAPT.

As used herein, the term "SNCA" refers to the gene for alpha-synuclein (aSYN)

As use herein, the term "NAC" refers to the alpha-synuclein fragment known as the non-A4 component (NAC) of Alzheimer's disease amyloid.

As used herein, the term "prion" refers to an infectious agent composed of protein in a misfolded form.

As used herein, the term "TSE" refers to any form or variety of a transmissible spongiform encephalopathy.

As used herein, the terms "alpha-synuclein" and "aSYN" are synonymous.

As used herein, the term "transmissible spongiform encephalopathy" and "TSE" are synonymous.

As used herein, the term "SOD1" refers to Superoxide dismutase (SOD1), which is an enzyme that in humans is encoded by the SOD1 gene, located on chromosome 21.

As used herein, the term "PD" refers to Parkinson's Disease.

As used herein, the term "DS" refers to Down Syndrome.

As used herein, the term "iron regulatory protein" is synonymous with "IRP"

As used herein, the term "iron-responsive element" is synonymous with "IRE".

As used herein, the term "HTT" refers to huntingtin or the Huntington protein.

As used herein, "TDP43" refers to the TAR-DNA binding protein TDP43.

As used herein, "C9orf72" refers to the C9orf72 protein found in many regions of the brain.

As used herein, the term "neurotoxic aggregating protein" refers to a protein or family of proteins that has neurotoxic effect upon accumulating in a tissue of the brain, such as the brain tissue. Non-limiting examples of neurotoxic aggregating proteins are APP, As, SOD1, SNCA, NAC, TSE amyloid plaque, HTT, Tau, TDP43 and C9orf72.

As used herein, the terms "protein", "peptide" and "polypeptide" are used interchangeably and refer to a compound comprised of amino acid residues covalently linked by peptide bonds.

By the term "specifically binds," as used herein, is meant a molecule, such as an antibody or a small molecule, which recognizes and binds to another molecule or feature, but does not substantially recognize or bind other molecules or features in a sample.

The phrase "inhibit" as used herein means to reduce a molecule, a reaction, an interaction, a gene, an mRNA, and/or a protein's expression, stability, function, or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function, and activity, e.g., antagonists.

"Effective amount" or "therapeutically effective amount" are used interchangeably herein, and refer to an amount of a compound, formulation, material, or composition, as described herein effective to achieve a particular biological result. Such results may include, but are not limited to, the treatment of a disease or condition as determined by any means suitable in the art.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary, and topical administration.

"Pharmaceutically acceptable" refers to a material(s) which are compatible with the activity of the compound useful within the invention and which are physiologically acceptable to the patient (e.g., human) from a pharmacological/toxicological point of view and to the manufacturing pharmaceutical chemist from a physical/chemical point of view regarding composition, formulation, stability, patient acceptance and bioavailability.

"Pharmaceutical acceptable carrier" refers to a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the term "salt" embraces addition salts of free acids or free bases that are compounds useful within the invention. Suitable acid addition salts may be prepared from an inorganic acid or from an organic acid. Examples of inorganic acids include hydrochloric, hydrobromic, hydriodic, nitric, carbonic, sulfuric, phosphoric acids, perchloric and tetrafluoroboronic acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable base addition salts of compounds useful within the invention include, for example, metallic salts including alkali metal, alkaline earth metal and transition metal salts such as, for example, lithium, calcium, magnesium, potassium, sodium, and zinc salts. Acceptable base addition salts also include organic salts made from basic amines such as, for example, N,N'-dibenzylethylenediamine, chloroprocaine, choline, diethanolamine, ethylenediamine, meglumine (N-methyl-glucamine) and procaine. All of these salts may be prepared by conventional means from the corresponding free base compound by reacting, for example, the appropriate acid or base with the corresponding free base.

An "individual", "patient", or "subject", as that term is used herein, includes a member of any animal species including, but are not limited to, birds, humans and other primates, and other mammals including commercially relevant mammals such as cattle, pigs, horses, sheep, cats, and dogs. Preferably, the subject is a human.

The term "treat" or "treating" as used herein means reducing the frequency with which symptoms are experienced by a subject or administering an agent or compound to reduce the frequency and/or severity with which symptoms are experienced. As used herein, "alleviate" is used interchangeably with the term "treat." Treating a disease, disorder or condition may or may not include complete eradication or elimination of the symptom. The term "therapeutic" as used herein means a treatment and/or prophylaxis of a condition or disease state as described herein.

As used herein, the term "infection" means a bacterial, viral, fungal, protozoan, or parasitic agent that has infiltrated a mammal (e.g., human) and thereby infected the mammal.

DETAILED DESCRIPTION OF THE INVENTION

Figure 1:
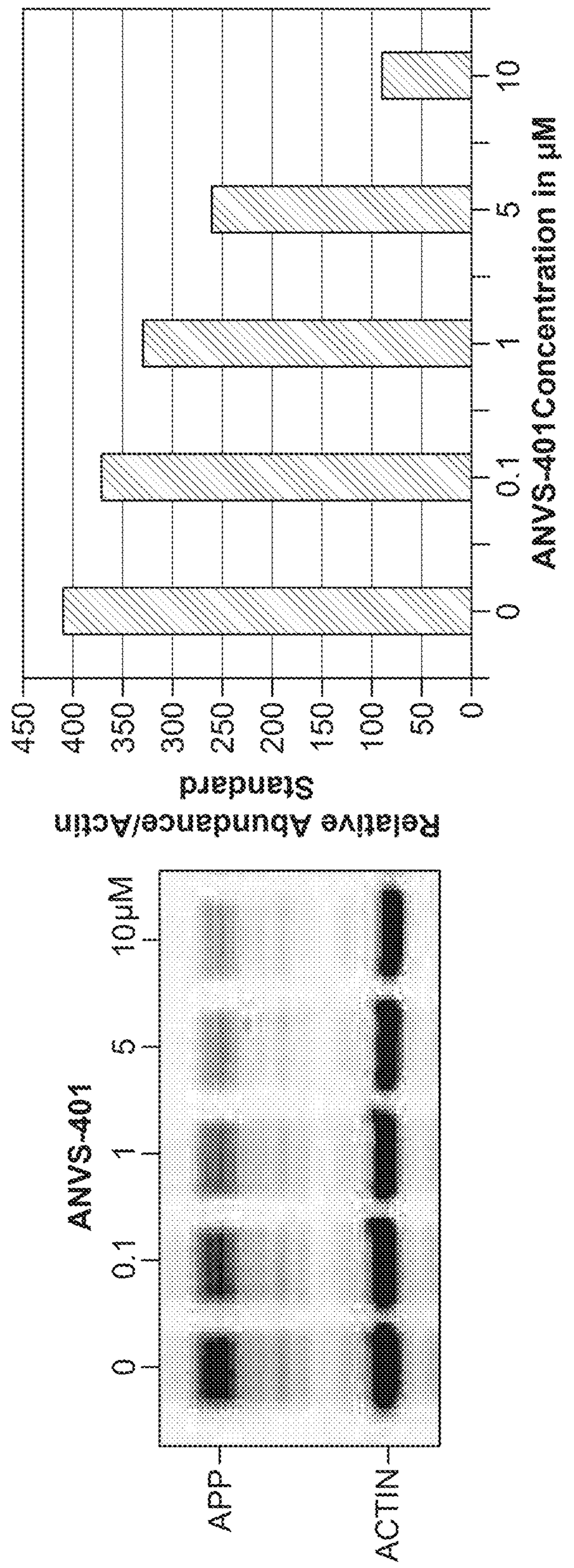
FIG. 1 is a Western blot and a graph showing that v lowers APP in vitro in a dose-dependent manner in SH-SY-5Y human neuroblastoma cells.

Many of the infections caused by viruses, bacteria, fungi, protozoa, or parasites encompassed herein do not initially cause neurological damage to the brain or central nervous system. Other such infections directly attack the brain or the central nervous system. In certain embodiments, the treatment of the present invention is initiated to the human(s) after they have been infected by a virus, bacterium, fungus, protozoa or parasite that can cause neurological damage, but prior to the infection directly or indirectly causing a neurological disorder or a neurodegenerative disease.

Infections

Viral, bacterial, fungal, protozoan, or parasitic infections can cause direct nerve damage by increasing iron levels, causing high levels of neurotoxic proteins which than activate the toxic cascade leading to nerve cell injury and death. They can also cause indirect nerve damage by provoking autoimmune disorders in which specialized cells and antibodies of the immune system attach to a mammal (e.g., the human body's) own tissues. These attacks typically cause destruction of the myelin sheath (axon) of the nerve. This can result in toxic encephalopathy and severe demyelinating lesions.

Infections of the nervous system are among the most difficult infections in terms of the morbidity and mortality posed to patients, and thereby require urgent, accurate diagnosis and treatment. Infections of the central nervous system (CNS) pose unique challenges to physicians, due to both the potential morbidity and mortality that they cause as well as the inherent difficulties involved in their treatment.

Infections can also be an unrecognized cause for peripheral nervous system (PNS) disease. PNS disease related to infection can cause severe neurological injury, either due to direct effects of the microbe or due to secondary immune overactivation. Neurological injuries may present, e.g., as acute inflammatory demyelinating polyneuropathy, mononeuropathy multiplex, cranial neuropathy, distal symmetric polyneuropathy, and the like.

Infections of the brain that may be inhibited, treated, prevented, etc. by the methods of the present invention include but are not limited to bacterial meningitis (e.g., *Streptococcus pneumonia* (causing pneumococcal meningitis), *Neisseria meningitidis* (causing meningococcal meningitis), and *Haemophilus* influenza type b (Hib)), toxoplasmosis (caused by *Toxoplasma gondii*), cerebral cysticercosis (caused by pork tapeworm), trichinoisis (caused by roundworm *Trichinella spiralis*), Lyme disease (caused by *Borrelia burgdorferi*), coccidioidal meningitis (caused by Cocidioides soil fungal spores), *Cryptococcus* (caused by fungal spores in soil), tuberculosis (caused by *Mycobacterium tuberculosis*), Cerebral abscess (caused by a complication of chronic sinus or middle-ear infections or the distant spread of the infection from somewhere else (such as a lung abscess or pneumonia), Spinal abscess (caused by various bacteria), West Nile virus and other members of the encephalitis-causing virus family (St. Louis encephalitis, western equine and Eastern equine encephalitis, and La Crosse encephalitis), Herpes viral family (herpes simplex types 1 and 2, varicella zoster, Epstein-Barr, cytomegalovirus), Poliomyelitis (caused by a small poliovirus), Rubella (caused by the rubella virus), Mumps and measles, Rabies, AIDS and HIV (caused by human immunodeficiency virus, HIV), Zika virus, Coronaviruses (e.g., severe acute respiratory syndrome CoV 2 (SARS-CoV-2), and the like.

Following is a list of representative infections shown to have neurological or neurodegenerative effects (Melissa Conrad Stöppler, MD, Chief Medical Editor Medicine Healthy; Symptoms and Signs of Brain Infection).

AIDS and HIV encephalitis is caused by the human immunodeficiency virus (HIV). HIV can directly infect the central nervous system, causing a range of neurologic conditions. The most common is so-called AIDS dementia. It is characterized by the slow onset of behavioral, intellectual, and motor impairment. Early symptoms include confusion, loss of libido, social withdrawal, decreased concentration, poor balance, and weakness. Psychiatric problems are common. HIV positive people have a very high rate of developing Alzheimer's disease later in life.

Cerebral cysticercosis is caused by the pork tapeworm. Depending on the stage of the disease, symptoms could be mild to severe meningitis, seizures, or even sudden death.

The members of herpes virus family (herpes simplex types 1 and 2, varicella zoster, Epstein-Barr, as well as cytomegalovirus) can enter the central nervous system from the peripheral nervous system (along the nerves outside of the brain and spinal cord), where they reside, and cause severe illness such as fulminant meningitis, encephalitis, or myelitis. Symptoms of specific infection can include psychiatric features and multiple seizures in herpes simplex 1, radicular symptoms (compression of nerve roots at the spinal column; numbness and tingling of the arms or legs) with urinary retention, and long-term herpes infections of the brain can lead to neurodegenerative diseases, such as Alzheimer's disease.

Gingivitis is caused by *Porphyromonas gingivalis*, the keystone pathogen in chronic periodontitis. It was identified in the brain of Alzheimer's patients. Toxic proteases of the bacterium called gingipains were also identified in the brain of Alzheimer's patients and their levels correlated with tau and ubiquitin pathology. Gingipains were neurotoxic in vivo and in vitro, exerting detrimental effects on tau, a protein needed for normal neuronal function, but toxic in certain situations. This caused neuroinflammation and neurodegeneration leading to Alzheimer's disease (Domini et al, *Science Advances* 23 Jan. 2019: Vol. 5, no. 1, eaau3333; DOI: 10.1126/sciadv.aau3333; *Porphyromonas gingivalis* in Alzheimer's disease brains: Evidence for disease causation and treatment with small-molecule inhibitors)

Lyme disease is caused by the bacterium *Borrelia burgdorferi*, which infects and multiplies inside of ticks of the *Ixodes* species. Then it is transmitted to humans by the tick bite. If untreated, the disease can have serious complications, which include various neurologic problems. Some patients with untreated Lyme disease and neurologic complications developed short-term memory problems and other cognitive deficits and may progress to Alzheimer's disease.

Mumps and measles are both caused by viruses. Young children are most commonly affected. Complications may include viral meningitis or encephalitis in varying degrees of severity.

Meningitis: Three types of bacteria are the most common causes: *Streptococcus pneumonia, Neisseria meningitidis, Haemophilus* influenza type b, and newborns are usually infected with coliform bacteria such as *Escherichia coli* or *Listeria.*

Coccidioidal meningitis is a severe complication of coccidiomycosis, a common fungal infection in the southwestern U.S. The meningitis, in addition to the typical signs and symptoms, is most commonly complicated by the presence of a hydrocephalus. Additionally, the inflammatory changes of the brain and its great vessels could cause symptoms similar to those of a stroke.

An uncommon causative agent of meningitis, affecting almost exclusively immunocompromised people, is a fungus from the *Cryptococcus* family. If left untreated, the patient has severe complications with permanent brain damage, hearing loss, and coma.

Poliomyelitis is caused by a small poliovirus. The spread of virus in the nervous system leads to paralysis, coma, and arrest of the respiratory and cardiac muscle.

Rabies is another viral infection. The virus causes a severe form of encephalitis and myelitis. It may cause initial flu-like symptoms, very high fever, extreme restlessness, hypersensitivity to touch, general convulsions, total body paralysis, bizarre hallucinations, excessive flow of saliva, gradual paralysis, coma, and almost invariably death.

Rubella is caused by the rubella virus. The consequences of this disease, affecting the unborn fetus infected during the first trimester of pregnancy, can be devastating.

Toxoplasmosis is caused by the parasite *Toxoplasma gondii*. The symptoms are similar to a mild form of bacterial meningitis. More than 50% of affected infants die within a few weeks after birth. The disease also is severe in someone with a weakened immune system.

Trichinosis is caused by the roundworm *Trichinella spiralis*. An infected person may have symptoms similar to encephalitis with confusion and delirium. Coma, seizures, paralysis, and other signs of neurologic loss are found in more severe forms.

Tuberculosis, caused by *Mycobacterium tuberculosis*, can spread through the lymphatic system to the CNS and causes neurologic deficits, such as visual impairment, focal weakness and numbness, and unstable gait with paralysis.

The West Nile virus and other members of the encephalitis-causing virus family (St. Louis encephalitis, western equine and eastern equine encephalitis, and La Crosse encephalitis) are usually spread by bites of ticks, mosquitoes, and flies. The virus itself, as well as the host's immune response, disrupt normal function of nerve cells, especially in the gray matter of the brain. This leads to various cognitive and psychiatric signs including confusion, lethargy, problems with coordination, and possible seizures.

Infection with Zika virus has been in the recent news due to a significant increase in the birth of babies with head deformities (microcephaly) and various neurologic complications in babies born to mothers infected with this virus. Very few patients infected with Zika virus develop a rare late neurologic complication known as a Guillain-Barré syndrome. This potentially fatal condition is triggered by a severe autoimmune reaction to the central and peripheral nervous system. It is characterized by progressively worsening weakness and paralysis of the muscles of the entire body, painful sensations in the extremities, and involvement of the nerves that supply the head and neck.

One recent example of viral infection affecting the brain is the 2019 Novel Coronavirus (2019-nCoV, now known as SARS-CoV-2), which was identified as the cause of an outbreak of respiratory illness. Coronaviruses are a large family of viruses, some causing illness in people and others in animals. For confirmed SARS-CoV-2 infections, symptoms have included fever, cough, and shortness of breath.

Additionally, various reports indicate that a significant proportion of patients with SARS 0 CoV□2 show neurologic symptoms, such as headache, nausea, vomiting, as well as loss of taste and smell and in rare cases even encephalitis (Li, 2020; Yeager 2020; Filatov, 2020). Also, new CT and MRI images published in Radiology (Mar. 31, 2020) of an infected patient with acute necrotizing encephalopathy (ANE) indicate an "intracranial cytokine storm" (Poyiadji 2020). Cytokine storm syndrome occurs when immune cells overproduce to fight off infection, potentially damaging the organ and, in the brain, resulting in breakdown of the blood brain barrier. It is believed that these neurologic symptoms in SARS-CoV-2 infected patients, indicate that the virus invades the central nervous system such as was previously reported for SARS-CoV or MERS (Li 2012, 2013). The Department of Radiology, Henry Ford Health System reported the first presumptive case of SARS-CoV-2 (COVID-19)-associated acute necrotizing hemorrhagic encephalopathy (Poyiadji, et al., 2020 COVID-19-associated Acute Hemorrhagic Necrotizing Encephalopathy, incorporated by reference).

Clinicians treating SARS-CoV-2 infected patients have begun to recognize that the virus in a significant proportion of patients can manifest in neurological issues including, but not limited to, brain inflammation, hallucinations, seizures, cognitive deficits and loss of smell and taste. Some neurologists have hypothesized that the fatal breathing problems caused by SARS-CoV-2 may be in part caused by malfunction of the brainstem secondary to the infection of the human patient by the virus. To date, scientists have been unable to determine whether these neurological issues are caused directly by the virus or by the body's immune response to the virus. (See, e.g., The Wall Street Journal, "Cases Show Disease's Effect on the Brain", Apr. 15, 2020).

Pathogens such as the viral and bacterial infections identified above need iron for survival, so high iron levels are common in such infections. Ongoing research supports the conclusion that microorganisms have developed mechanisms for stealing ferritin (the protein that stores iron and releases it) from different organs and tissues of the body. High iron levels increase the translation of neurotoxic proteins leading to the toxic cascade that causes nerve cell death and neurodegeneration.

Iron Levels in Brain, Infections, Neurodegeneration and Other Conditions: Bacterial, Viral, Fungal, Protozoan or Parasitic Infections Increase Iron; High Iron Causes Over-Translation of Neurotoxic Proteins; Neurotoxic Proteins Lead to Nerve Cell Death In certain embodiments, the invention is directed to maintaining (heavy) metal homeostasis in a human(s) who is at risk of exposure to infection by or is infected by a virus, bacterium, fungus, protozoan or parasite that can cause neurological damage, and thereby inhibiting or preventing neurological damage in the human by maintaining (heavy)

metal homeostasis in the human(s) in accordance with the treatment (administration of butanetap) as set forth in this paragraph and herein. In certain embodiments, the treatment of the present invention is initiated to human(s) who has been infected by a virus, bacterium, fungus, protozoan or parasite that can cause neurological damage, prior to the infection directly or indirectly causing a neurological disorder or neurological damage (e.g., a neurodegenerative disease).

Appropriate iron levels are especially important in the brain. Adequate iron levels are required for the increased respiration, neurotransmitter production, and myelinogenesis. Iron deficiency may have deleterious effects on neurotransmission, myelination, and dopamine receptor and transporter functions. On the other hand, excess iron concentrations are particularly harmful because the highly oxidative microenvironment of the brain lends itself to the production of ROS. Although brain iron regulation and uptake are not fully understood, many of the proteins involved in iron homeostasis throughout the body are also present in the brain. Increased brain iron levels have been observed in viral, bacterial, and other infections as well as in Alzheimer's disease and Parkinson's disease. Abnormal iron metabolism has been implicated in the pathogenesis of neurodegeneration.

Iron is essential for life processes. It has essential roles in the body such as red blood cell and hemoglobin formation, ATP synthesis in every cell of the body, as well as its need for the formation of the antioxidant catalase. While iron is essential for life, iron is a very toxic element that requires sufficient iron binding proteins such as transferrin, ferritin and lactoferrin. Excess iron accumulation can become a primary cause of oxidative stress and free radical activity.

One of the causes of nerve cell injury is infection by a virus, bacterium, fungus, protozoa, or parasite and one indicator of possible pathogenic infections is high iron levels. Host pathogens need iron for survival. (Drakesmith H & Prentice; A. Nat Rev Microbiol. 2008 July; 6(7):541-52. doi: 10.1038/nrmicro1930. Viral infection and iron metabolism). There is evidence that increased levels of iron decrease certain immune cell scavenging abilities, such as neutrophils, and T cells. Simultaneously, increased levels of iron become a source of replication for certain pathogens and increase their growth.

There is ongoing research that demonstrates that microorganisms have developed mechanisms for stealing ferritin (the protein that stores iron and releases it) from different organs and tissues of the body (McEvoy; Metabolic Healing 2018; Iron toxicity & pathogenic infections). For example, listeria obtains ferritin from neurons, epithelial cells, macrophages, and intestinal cells. The parasite *Entamoeba histolytica* steals ferritin from the blood, brain, lungs, and intestines. *Candida Albicans* can heist ferritin from the GI tract to survive.

When a nerve cell becomes injured, iron flows into the cell. High iron levels increase the translation of neurotoxic proteins, leading to impairment of axonal transport, inflammation, and nerve cell death.

For example, Rogers, et al. (Biochem Soc Trans. 2008 December; 36 (Pt 6): 1282-7, "Iron and the translation of the amyloid precursor protein (APP) and ferritin mRNAs: riboregulation against neural oxidative damage in Alzheimer's disease.") reported that the essential metals iron, zinc and copper deposit near the Aβ plaques in the brain cortex of AD patients. In health, ubiquitous APP is cleaved in a non-amyloidogenic pathway within its Aβ domain to release the neuroprotective APP ectodomain, soluble APPs. To adapt and counteract metal-catalysed oxidative stress, as during reperfusion from stroke, iron and cytokines induce the translation of both APP and ferritin (an iron storage protein) by similar mechanisms. Rogers, et al. reported that APP was regulated at the translational level by IRE (iron-responsive element) RNA stem-loops in the 5' untranslated region of APP mRNA, and that the APP IRE is homologous with the canonical IRE RNA stem-loop that binds the iron regulatory proteins (IRP1 and IRP2) to control intracellular iron homoeostasis by modulating ferritin mRNA translation and transferrin receptor mRNA stability. The APP IRE interacts with IRP1 (cytoplasmic cis-aconitase), whereas the canonical H-ferritin IRE RNA stem-loop binds to IRP2 in neural cell lines, and in human brain cortex tissue and in human blood lysates. The same constellation of RNA-binding proteins [IRP1/IRP2/poly(C) binding protein] control ferritin and APP translation with implications for the biology of metals in Alzheimer's Disease.

Iron levels have also been implicated in cancer. Researchers have reported that iron is critical for growth of tumors (Torti, et al. "Ironing out cancer", Cancer Res., 71 (2011), pp. 1511-1514). Tumor cells can satisfy their increased need for iron by increasing TfR1 expression as well as reducing ferritin and ferroportin expression (See, e.g., Cozzi, et al. "Overexpression of wild type and mutated human ferritin H-chain in HeLa cells: in vivo role of ferritin ferroxidase activity", J. Biol. Chem., 275 (2000), pp. 25122-25129; Kakhlon, et al., "Repression of ferritin expression increases the labile iron pool, oxidative stress, and short-term growth of human erythroleukemia cells", Blood, 97 (2001), pp. 2863-2871; Cozzi, et al., "Analysis of the biologic functions of H- and L-ferritins in HeLa cells by transfection with siRNAs and cDNAs: evidence for a proliferative role of L-ferritin", Blood, 103 (2004), pp. 2377-2383; Baldi, et al., "Ferritin contributes to melanoma progression by modulating cell growth and sensitivity to oxidative stress", Clin. Cancer Res., 11 (2005), pp. 3175-3183; Pinnix, et al., "Ferroportin and iron regulation in breast cancer progression and prognosis", Sci. Transl. Med., 2 (2010), p. 43ra56). IRP2 has also been shown to have a role in cell proliferation. For example, researchers have demonstrated that IRP2 overexpression in H1299 lung cancer cells stimulated their ability to form tumors when grown as xenografts in immunodeficient mice, whereas overexpression of IRP2 lacking the 73-amino acid domain suppressed tumor xenograft growth, suggesting a unique function for this domain (Maffettone, "Tumorigenic properties of iron regulatory protein 2 (IRP2) mediated by its specific 73-amino acids insert", PLoS One, 5 (2010), p. e10163). In contrast, researchers have also demonstrated that overexpression of IRP1 in H1299 lung cancer cells suppressed tumor xenograft growth in mice (Chen, et al., "Overexpression of iron regulatory protein 1 suppresses growth of tumor xenografts", Carcinogenesis, 28 (2007), pp. 785-791).

Neurodegenerative Diseases: Bacterial, Viral, Fungal, Protozoan or Parasitic Infections Increase Iron: High Iron Causes Over-Translation of Neurotoxic Proteins; Neurotoxic Proteins Lead to Nerve Cell Death Neurodegenerative diseases generally affect abstract thinking, skilled movements, emotional feelings, cognition, memory, and other abilities. Despite differences in clinical symptoms and disease progression, disorders from this group share key common features: most of them have both sporadic and inherited origins, all of them appear later in life, and their pathology is characterized by neuronal loss and synaptic abnormalities. Until recently, no common molecular mechanism had been identified among these diseases. However, various neurodegenerative diseases, such as Alzheimer's disease (AD), Parkinson's disease (PD), Frontotemporal Dementia (FTD), Huntington's disease (HD), transmissible spongiform encephalopathies (TSEs), and amyotrophic lateral sclerosis (ALS), have been shown to share a common cause and pathological mechanism—the overexpression, misfolding, aggregation and accumulation of proteins in the brain, resulting in neuronal apoptosis. The hallmark feature of conformational disorders is that at high concentrations a particular protein folds into a stable alternative conformation, which in most cases results in its aggregation and accumulation in tissues as fibrillar deposits. These deposits have similar morphological, structural, and staining characteristics. Multidisciplinary studies strongly support this shared cause and pathological mechanism, suggesting that there may be a common therapy for these devastating disorders.

Neurotoxic aggregating proteins have not only a common aggregating pathway, but also common regulatory pathways for their transcription and translation. While their transcription is activated by copper and/or zinc ions (Bush et al., 2003, Proc. Natl. Acad. Sci. U.S.A. 100(20):11193-94), their translation is upregulated by iron and down-regulated by IRP1. Specifically, their mRNAs are regulated via the 5'-untranslated region (5'UTR) of their transcript, which folds into a unique RNA stem loop with a CAGUGN apical loop similar to that encoded in the canonical IRE of L- & H-ferritin mRNAs. IRP1 binds to this IRE stem look and inhibits the translation of the mRNA by the ribosome (Cho et al., 2010, J. Biol. Chem. 285(41):31217).

Examples of neurotoxic aggregating proteins are Aβ (amyloid-β peptide, a fragment of APP), Tau, alpha-synuclein (aSYN), transmissible spongiform encephalopathy (TSE) prions SOD (super oxide dismutase) proteins, huntingtin (HTT), TDP43 and c9orf72.

Even though tau is not a member of the iron regulated neurotoxic protein family, it is overexpressed and aggregates in a number of tauopathies. Conditions in which neurofibrillary tangles are commonly observed include: Alzheimer's disease, progressive supranuclear palsy, dementia pugilistica, chronic traumatic encephalopathy, frontotemporal dementia and parkinsonism linked to chromosome 17, Lytico-Bodig disease (Parkinson-dementia complex of Guam), Tangle-predominant dementia, with neurofibrillary tangles similar to AD, but without plaques. Tau deposits tend to appear in the very old, Picks disease and a number of other neuropathies. Tau's fibrillary tangles are found in most neurodegenerative disorders.

It has been found that a hallmark of Parkinson's disease—clumps of alpha-synuclein, called Lewy Bodies—are found not only in the mid-brain but also in the brain stem, the gut, and the olfactory bulb. Lewy bodies and aSYN aggregates are present in multiple nerves from the periphery to the brain and, while motor symptoms are associated with Lewy bodies in the brain, non-motor symptoms are associated with aggregates in the periphery. Non-motor symptoms in general are experienced by all people with PD before any motor sign of the disease appears. Lewy bodies are also found in several other brain disorders, including dementia with Lewy bodies (DLB). Evidence suggests that dementia with Lewy bodies, Parkinson's disease and Parkinson's disease dementia may be linked to the same underlying abnormalities in brain processing of alpha-synuclein. Many of those afflicted with both dementia with Lewy bodies and Parkinson's disease dementia also have plaques and tangles—which are the hallmark of Alzheimer's disease. Thus, there is an interrelationship between the Parkinson's disease-related protein alpha-synuclein and the Alzheimer's AB-amyloid plaque protein.

Applicant's previous U.S. application Ser. No. 15/987,420, filed May 23, 2018, hereby incorporated by reference in its entirety, is directed to a method of maintaining (heavy) metal homeostasis in healthy humans or restoring (heavy) metal homeostasis in sick human patients, comprising or consisting of chronically administering to the human(s) a pharmaceutical composition comprising or consisting of a therapeutically effective amount of butanetap, active metabolites of butanetap, therapeutically effective analogues of butanetap, pharmaceutically acceptable salts and complexes thereof-together with one or more pharmaceutically acceptable excipients. In certain preferred embodiments, the metal is iron. The method inhibits, prevents or treats Alzheimer's disease, Tauopathies, Frontotemporal Dementia, Down Syndrome, Parkinson's and alpha-synucleopathies, Prion's disease, Huntington's disease, Amyloid Lateral Sclerosis, and other dementias and neurodegenerative disorders, as well as other disease states including but not limited to cancer, cardiovascular, heart, lung, kidney and/or liver homeostasis diseases, and the like by treating metal (e.g., iron) dis-homeostasis in various tissues (e.g., brain, heart, lung, kidney, liver, etc.).

Butanetap

Butanetap, developed by QR Pharma, Inc. (now Annovis Bio, Inc.), is a small molecule that lowers soluble APP protein levels through a post-transcriptional mechanism. Butanetap is also known as (+)-Phenserine. Butanetap is the steroisomer of Phenserine (−)-N-phenylcarbamoyl eseroline), which reached clinical assessment for AD as an anticholinesterase inhibitor. Phenserine is an AChE inhibitor which has been investigated as being suitable as an agent for therapy for cognitive impairments associated with aging and Alzheimer's disease (U.S. Pat. No. 5,409,948). Due to its high cholinomimetic side effects, phenserine failed in 3 phase 3 clinical studies.

As used herein, the term "butanetap" refers to (3aR)-1,3a,8-trimethyl-1,2,3,3a,8,8a-hexahydropyrrolo[2,3-b]indol-5-yl phenylcarbamate, with the chemical structure shown in Formula IV below, at a chemical purity of at least 90%, preferably at least 95%, at least 98%, at least 99%, at least 99.5%, at least 99.9% or 100%, having the chemical structural as follows:

(IV)

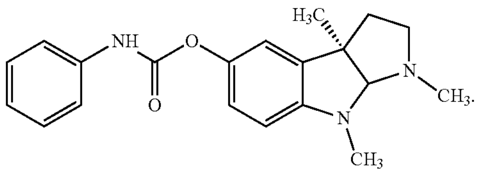

The term "chemical purity" as applied to (3aR)-1,3a,8-trimethyl-1,2,3,3a,8,8a-hexahydropyrrolo[2,3-b]indol-5-yl phenylcarbamate or a pharmaceutically acceptable salt of butanetap means the percent by weight of (3aR)-1,3a,8-trimethyl-1,2,3,3a,8,8a-hexahydropyrrolo[2,3-b]indol-5-yl phenylcarbamate or the pharmaceutically acceptable salt of butanetap in terms of (3aR)-1,3a,8-trimethyl-1,2,3,3a,8,8a-hexahydropyrrolo[2,3-b]indol-5-yl phenylcarbamate or the pharmaceutically acceptable salt of butanetap and other chemical impurities, e.g., its (−)-enantiomer, that may be present.

The invention also encompasses active metabolites of butanetap. Active metabolites have previously been identified and include, for example, "$N^1$-nor-butanetap" (which refers to (3aR)-3a,8-dimethyl-1,2,3,3a,8,8a-hexahydropyrrolo[2,3-b]indol-5-yl phenylcarbamate) or a salt thereof; "$N^8$-nor-butanetap" (which refers to (3aR)-1,3a-dimethyl-1,2,3,3a,8,8a-hexahydropyrrolo[2,3-b]indol-5-yl phenylcarbamate) or a salt thereof; and "$N^1$,$N^8$-nor-butanetap" (which refers to (3aR)-3a-methyl-1,2,3,3a,8,8a-hexahydropyrrolo [2,3-b]indol-5-yl phenylcarbamate) or a salt thereof.

Butanetap is a selective inhibitor of amyloid precursor protein (APP) production and has potential utility as a disease modifying treatment for AD (Cullen 2006; Utsuki 2006; Lahiri 2007). butanetap was discovered at the National Institute on Aging and was selected from a series of structurally related compounds designed for APP specificity with no or minimal acetylcholinesterase inhibitory activity. Butanetap was shown to reduce APP and consequently beta-amyloid (Aβ) production in relevant preclinical in vitro and in vivo studies. Maccecchini, et al., "*Butanetap (Posiphen) as a Candidate Drug to Lower CSF Amyloid Precursor Protein, Amyloid-β Peptide and τ Levels: Target Engagement, Tolerability and Pharmacokinetics in Humans*", J. Neurosurg. Psychiatry 2012; 83:894-902, hereby incorporated by reference, reported the results of a study of butanetap single and multiple ascending dose phase 1 randomized, double blind, placebo-controlled safety, tolerance, pharmacokinetic studies were undertaken in 120 healthy human volunteers to define a dose that was then used in a small non-randomised study of five MCI subjects. Butanetap doses up to 4×60 mg daily×10 days were well tolerated. In plasma butanetap, at all doses, was absorbed rapidly (Tmax=1.2 to 1.7 h) and cleared from the circulation biphasically (terminal half-life of 4.3-4.7 h). Butanetap proved well tolerated and significantly lowered CSF levels of sAPPα, sAPPβ, t-tau, p-tau, and specific inflammatory markers, and demonstrated a trend to lower CSF $Aβ_{42}$. Butanetap's activity is also described in Applicant's U.S. Pat. No. 10,383,851, hereby incorporated by reference.

In 2004, it was reported that Phenserine was most efficient to block translation of APP mRNA under conditions of intracellular iron chelation with desferrioxamine, suggesting that this anticholinesterase operated through an iron (metal)-dependent pathway at the APP 5'-UTR site. (Venti, et al. "The Integrated Role of Desferrioxamine and Phenserine Targeted to an Iron-Responsive Element in the APP-mRNA 5-Untranslated Region", Ann. N.Y. Acad. Sci. 1035: 34-48 (2004), hereby incorporated by reference in its entirety. This would mean that Phenserine works at low iron levels. However, this was exactly the opposite of what was found by the present inventor.

The present inventor was able to reproduce results indicating that butanetap inhibits APP and aSYN in neuroblastoma cells. However, it has now been unexpectedly found that butanetap does not inhibit translation of neurotoxic aggregating proteins in healthy mouse brain, or in fully differentiated healthy resting nerve cells. Under iron or metal-homeostasis, butanetap does not increase the binding of APP or aSYN mRNA to IRP1. Therefore, the original data concerning the effects of butanetap working under all conditions is wrong. (See, e.g., Lahiri, et al., "The Experimental Alzheimer's Disease Drug butanetap [(+)-Phenserine] Lowers Amyloid-β Peptide Levels in Cell Culture and Mice", J. Pharmacol. Ther. 320:386-396, 2007 (hereby incorporated by reference)). It only works in stressed cells, dividing cells and sick cells, e.g., those cells that have high levels of iron.

Butanetap augments the binding of APP mRNA IRE to IRP1 under high iron conditions and prevents APP from being translated excessively, restoring homeostasis. The same mechanism works for all neurotoxic aggregating proteins tested to date: Butanetap works under iron-dishomeostasis to restore homeostasis.

It has further been surprisingly discovered that butanetap does not have any effect on normal, healthy cells—where the level of iron is also normal. Once this discovery was made, the activity of butanetap in a variety of cells made sense: in fully differentiated nerve cells that do not divide, administration of butanetap elicits no effect. In dividing cells, the iron levels go up and down with the cell cycle. Butanetap inhibits neurotoxic aggregating proteins in stem cells (dividing cells), but not in the differentiated neurons derived from the same. In the hippocampus of the brain of AD mice, where plaque accumulation occurs, butanetap has been found to inhibit neurotoxic aggregating proteins. Areas where plaque accumulation occurs contain stressed and sick cells, which have high iron levels. On the other hand, areas where plaque is not typically found (until late in the disease state), such as the cerebral cortex, do not have high levels of iron, and butanetap has now been found to not inhibit neurotoxic aggregating proteins in the cerebral cortex of transgenic AD and PD animals, although it inhibits these neurotoxic aggregating proteins in the hippocampus of AD animals and the enteric nerves of PD animals (i.e., in the gut), respectively.

Thus, the present invention is based on the fact that butanetap works only in dividing, sick or stressed cells, where iron levels are high. For purposes of the present invention, iron levels in vitro are defined as follows: about 1 uM or lower=low iron levels; about 3 to about 10 uM=normal iron levels; from about 10 to about 100 uM=high iron levels. Iron levels in vivo are very difficult to measure and there is a lot of disagreement among the experts in defining what a high level is, because of very little free iron in vivo in humans. Depending on the extraction conditions levels, the value can vary by more than, e.g., 10-fold. However, there is some consensus: from imaging studies, diseased tissues show about twice as much iron as healthy tissues, or an increase, e.g., from about 50% to about 100% as compared to healthy tissues. From actual measurements in normal substantia nigra wet weight: 0.3 uM/gram of brain; dry weight: 13 uM/gram comparing in vitro with in vivo, 1 uM is about 0.05 uM/gram; 10 uM is about 0.5 uM/gram; and 50 uM is about 2.5 uM/gram.

Applicant's previous U.S. application Ser. No. 15/987,420, hereby incorporated by reference, is directed in part to the treatment of healthy humans with chronic administration of effective amounts of butanetap, its active metabolites, and pharmaceutically acceptable salts and complexes thereof, as well as analogues thereof and similar compounds. Healthy humans can be treated with such drugs without any apparent effect—as long as they are healthy. It is only when cells in the body become stressed—e.g., have an abnormally high level of iron, that butanetap will have a therapeutic effect, which will be to return the cells to normal iron levels, thereby avoiding the toxic levels that are found in a variety of disease states and conditions. In Applicant's previous U.S. application Ser. No. 15/987,420, it was reported that the high iron levels in cells treated by the inventive methods include high iron levels caused by the onset of a neurodegenerative disease selected from the group consisting of Alzheimer's disease, Tauopathies, Parkinson's and alpha-synucleopathies, Prion's disease, Down Syndrome, Huntington's disease, Amyloid Lateral Sclerosis and other dementias and neurodegenerative disorders. Such dementias include, but are not limited to Vascular dementia, Dementia with Lewy bodies (DLB), Mixed dementia, Frontotemporal dementia, Creutzfeldt-Jakob disease, Normal pressure hydrocephalus, and Wernicke-Korsakoff Syndrome. That invention is directed in part to the administration of butanetap to healthy humans in order to prevent or control such neurological diseases which have not as yet afflicted them, as well as other conditions which can be treated or slowed from causing hallmark symptoms of the condition include traumatic brain injury, chronic traumatic encephalopathy (CPE), vascular dementia, posterior cortical atrophy (PCA), and the like. The present invention is directed to the administration of butanetap, etc. in order to inhibit, prevent or treat neurological damage (e.g., neurodegeneration) and neurological conditions or diseases in humans who are infected by a virus, bacterium, fungus, protozoan or parasite that can cause the same. Butanetap (or similar compounds as described herein) works in similar fashion as that described in U.S. Ser. No. 15/987,420, i.e., high iron levels in cells caused by the onset of a neurodegenerative disease in conjunction with a viral or bacterial infection in a human are treated by the inventive methods of treatment with agents as described herein, such as butanetap. Butanetap and these other agents in such circumstances improve axonal transport by inhibiting the neurotoxic proteins that kill nerve cells, e.g., in the brain. Further information concerning the administration of butanetap is found, e.g., in Applicant's earlier U.S. Pat. No. 10,383,851 and other patents issued in that patent family, also hereby incorporated by reference.

Active Analogs

In other embodiments, the methods of the present invention are practiced using a phenserine or phenserine-like compound, metabolite, enantiomer, or derivative thereof, known to those skilled in the art, such as those described in U.S. Pat. Nos. 5,171,750; 6,410,747; 6,683,105, 7,153,882; 7,786,162; 7,973,057; 8,258,172; 8,546,430; 8,691,864; and 8,853,253, all of which are incorporated by reference in their entireties.

In a broader sense, the invention is directed to the use of a compound having the Formula I or II as follows:

(I)

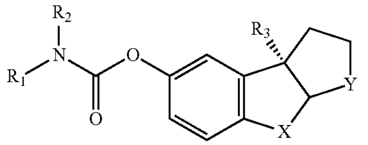

or (II)

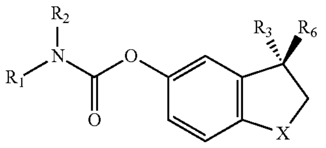

wherein $R_1$ and $R_2$ are, independently, hydrogen, branched or straight chain $C_1$-$C_8$ alkyl, substituted or unsubstituted aryl, heteroaryl, or aralkyl; $R_3$ is branched or straight chain $C_1$-$C_4$ alkyl or heteroalkyl or $C_4$-$C_8$ alkyl or heteroalkyl, or substituted or unsubstituted aryl; X and Y are, independently, O, S, alkyl, hydrocarbon moiety, $C(H)R_4$, or $NR_5$, wherein $R_4$ and $R_5$ are, independently, hydrogen, oxygen, branched or straight chain $C_1$-$C_8$ alkyl, $C_2$-$C_8$ alkenyl or $C_2$-$C_8$ alkynyl, aralkyl, or substituted or unsubstituted aryl; and $R_6$ is hydrogen; $C_1$-$C_8$ alkyl, $C_1$-$C_8$ alkenyl, $C_2$-$C_8$ alkynyl, aralkyl, or substituted or unsubstituted aryl, or $(CH_2)_nR_7$, where $R_7$ is hydroxy, alkoxy, cyano, ester, carboxylic acid, substituted or unsubstituted amino, and n is from 1 to 4.

The chiral center of compounds of Formula I and II is the carbon atom that has $R_3$ bonded to it. As depicted herein, the (+)-enantiomer has $R_3$ pointing behind the plane of the page. Although only the (+)-isomer is illustrated to save space, in other embodiments the compound having the Formula I or II can be the (+)-isomer, (−)-isomer, and mixtures of both isomers (e.g., racemic mixtures, including 1:1 racemic mixtures) of all of the compounds encompassed by the invention.

In certain embodiments, the compounds having the Formula I or II have an enantiomeric purity for the (+)-enantiomer of from 55 to 100%, desirably from 75 to 100%, more desirably from 85 to 100%, more desirably from 95 to 100%, and even more desirably 100%.

In certain preferred embodiments, wherein the compound having the Formula I or II is the substantially pure (+)-enantiomer.

In one embodiment, when the compound is Formula I, $R_3$ is methyl and is X is $NCH_3$.

In one embodiment, when the compound is Formula I or II, $R_3$ is not methyl. In particular embodiments, $R_3$ is a branched or straight chain alkyl or heteroalkyl group of 2, 3, 4, 5, 6, 7, or 8 carbons or substituted or unsubstituted aryl.

In another embodiment, when the compound is Formula I or II, Y is $C(H)R_4$ or X is O, S, or $C(H)R_4$.

In another embodiment, when the compound is Formula I, $R_3$ is methyl, X is $NCH_3$, and Y is $NCH_3$. In one embodiment, when the compound is Formula I, $R_3$ is methyl, X is $NCH_3$, Y is $NCH_3$, and $R_1$ is $C_1$-$C_8$ straight chain alkyl or benzyl and $R_2$ is hydrogen. In one embodiment, when the compound is Formula I, $R_3$ is methyl, X is $NCH_3$, Y is $NCH_3$, and $R_1$ is substituted or unsubstituted phenyl and $R_2$ is hydrogen. In one embodiment, when the compound is Formula I, $R_3$ is methyl, X is $NCH_3$, Y is $NCH_3$, and $R_1$ and $R_2$ are, independently, methyl or ethyl.

In another embodiment, when the compound is Formula I, $R_3$ is methyl, X is $NCH_3$, and Y is O. In one embodiment, when the compound is Formula I, $R_3$ is methyl, X is $NCH_3$, Y is O, $R_1$ is $C_1$-$C_8$ straight chain alkyl or benzyl, and $R_2$ is hydrogen. In one embodiment, when the compound is Formula I, $R_3$ is methyl, X is $NCH_3$, Y is O, and $R_1$ and $R_2$ are, independently, methyl or ethyl. In one embodiment, when the compound is Formula I, $R_3$ is methyl, X is $NCH_3$, Y is O, and $R_1$ is substituted or unsubstituted phenyl and $R_2$ is hydrogen.

In another embodiment, when the compound is Formula I, $R_3$ is methyl, X is $NCH_3$, and Y is S. In one embodiment, when the compound is Formula I, $R_3$ is methyl, X is $NCH_3$, Y is S, $R_1$ is $C_1$-$C_8$ straight chain alkyl or benzyl, and $R_2$ is hydrogen. In one embodiment, when the compound is Formula I, $R_3$ is methyl, X is $NCH_3$, Y is S, and $R_1$ and $R_2$ are, independently, methyl or ethyl. In one embodiment, when the compound is Formula I, $R_3$ is methyl, X is $NCH_3$, Y is S, $R_1$ is substituted or unsubstituted phenyl, and $R_2$ is hydrogen.

In another embodiment, when the compound is Formula I, $R_3$ is methyl, X is $NCH_3$, and Y is $NR_5$. In one embodiment, when the compound is Formula I, $R_3$ is methyl, X is $NCH_3$, and Y is $NR_5$, wherein $R_5$ is $—CH_2CH{=}CH_2$, $—CH_2CH_2Ph$, benzyl, or hydrogen.

In another embodiment, when the compound has the Formula I, $R_3$ is methyl, Y is $NCH_3$, and X is $NCH_3$, wherein $R_4$ is benzyl or hydrogen.

In another embodiment, when the compound is Formula I, $R_3$ is methyl, X is $NCH_3$, Y is $NR_5$, wherein each $R_4$ and $R_5$ is, independently, hydrogen or benzyl.

In another embodiment, when the compound is Formula I, $R_3$ is phenyl, X is $NCH_3$, and Y is $NCH_3$.

In another embodiment, when the compound is Formula I, $R_3$ is methyl, and X is $NCH_3$, and Y is not NH or $NHCH_2Ph$.

In some embodiments, when the compound is Formula I, $R_1$ and $R_2$ are independently, hydrogen, substituted or unsubstituted aryl, $R_3$ is straight chain $C_1$-$C_8$ alkyl, X and Y are independently $NR_5$, wherein $R_5$ is independently hydrogen or straight chain $C_1$-$C_8$.

In some embodiments, when the compound is Formula I, $R_1$ and $R_2$ are independently, hydrogen or unsubstituted aryl, $R_3$ is straight chain $C_1$-$C_8$ alkyl, X and Y are independently $NR_5$, wherein $R_5$ is independently hydrogen or straight chain $C_1$-$C_8$.

In some embodiments, when the compound is Formula I, $R_1$ is hydrogen, $R_2$ is unsubstituted aryl, $R_3$ is methyl, X and Y are independently $NR_5$, wherein $R_5$ is independently hydrogen or methyl.

In a certain preferred embodiment, when the compound is Formula I, $R_1$ is hydrogen, $R_2$ is phenyl, $R_3$ is methyl, X is $NCH_3$, and Y is $NCH_3$.

In other embodiment, when the compound is Formula I, $R_1$ is hydrogen, $R_2$ is phenyl, $R_3$ is methyl, X is $NCH_3$, and Y is NH.

In a certain preferred embodiment, when the compound is Formula I, $R_1$ is hydrogen, $R_2$ is phenyl, $R_3$ is methyl, X is NH, and Y is $NCH_3$.

In a certain preferred embodiment, when the compound is Formula I, $R_1$ is hydrogen, $R_2$ is phenyl, $R_3$ is methyl, X is NH, and Y is NH.

In another embodiment, when the compound is Formula II, $R_3$ is methyl, X is $C(H)CH_3$, and $R_6$ is $(CH_2)_2R_7$, where $R_7$ is a substituted or unsubstituted amino group.

In a certain preferred embodiment, when the compound is Formula II, $R_3$ is methyl, X is $NCH_3$, and $R_6$ is $(CH_2)_2R_7$, where $R_7$ is a substituted or unsubstituted amino group.

In a certain preferred embodiment, wherein the compound having the Formula II is the substantially pure (+)-enantiomer.

The invention also relates to the use of a compound having the Formula (III) as follows:

(III)

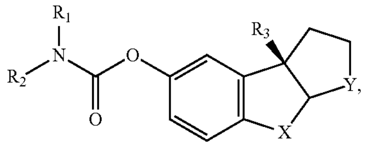

wherein $R_1$ and $R_2$ are, independently, hydrogen, branched or straight chain $C_1$-$C_8$ alkyl, substituted or unsubstituted aryl, heteroaryl, or aralkyl; $R_3$ is branched or straight chain $C_1$-$C_4$ alkyl or heteroalkyl or $C_4$-$C_8$ alkyl or heteroalkyl, or substituted or unsubstituted aryl; X is $NR_5$, wherein $R_5$ is $C_{2-8}$ alkenyl, $C_{2-8}$ alkynyl, or aralkyl, and Y is selected from $C(H)R_4$ or $NR_5$, wherein $R_4$ and $R_5$ are, independently, hydrogen, branched or straight chain $C_{1-8}$ alkyl or heteroalkyl, alkenyl, or $C_2$-$C_8$ alkynyl, aralkyl.

As depicted herein, the (−)-enantiomer has $R_3$ pointing in front of the plane of the page. Although only the (−)-isomer is illustrated to save space, in other embodiments the compound having the Formula (III) can be the (+)-isomer, (−)-isomer, and mixtures of both isomers (e.g., racemic mixtures, including 1:1 racemic mixtures) of all of the compounds encompassed by the invention.

In a certain preferred embodiment, wherein the compound having the Formula (III) is the substantially pure (−)-enantiomer.

In one embodiment, when the compound is Formula (III), X is $NR_5$, wherein $R_5$ is aralkyl.

In one embodiment, when the compound is Formula (III), X and Y are $NR_5$, wherein $R_5$ is aralkyl.

In one embodiment, when the compound is Formula (III), wherein X is $NR_5$, wherein $R_5$ is aralkyl, and Y is $NR_5$, wherein $R_5$ is branched or straight chain $C_{1-8}$ alkyl or heteroalkyl.

In one embodiment, when the compound is Formula (III), wherein $R_1$ is branched or straight chain $C_1$-$C_8$ alkyl, aralkyl or aryl, $R_2$ is hydrogen, branched or straight chain $C_1$-$C_8$ alkyl, substituted or unsubstituted aryl, or aralkyl; Y is $NR_5$, wherein $R_5$ is aralkyl; and X is $NR_5$, wherein $R_5$ is hydrogen, branched or straight chain $C_{1-8}$ alkyl or heteroalkyl.

In one embodiment, when the compound is Formula (III), wherein $R_1$ is branched or straight chain $C_1$-$C_8$ alkyl, aralkyl or aryl; $R_2$ is hydrogen, branched or straight chain $C_1$-$C_8$ alkyl; Y is $NR_5$ where $R_5$ is benzyl; and X is $NR_5$, wherein $R_5$ is hydrogen, branched or straight chain $C_{1-8}$ alkyl or heteroalkyl.

In one embodiment, when the compound is Formula (III), wherein $R_1$ is branched or straight chain $C_1$-$C_8$ alkyl, aralkyl or aryl; $R_2$ is hydrogen, branched or straight chain $C_1$-$C_8$ alkyl; Y is $NR_5$ where $R_5$ is benzyl; and X is $NR_5$, wherein $R_5$ is hydrogen.

In one embodiment, when the compound is Formula (III), wherein $R_1$ is para-halophenyl; Y is $NCH_3$; and X is $NR_5$, wherein $R_5$ is alkyl or aralkyl, wherein $R_1$ is not para-phenyl bromophenyl when $R_5$ is benzyl.

In one embodiment, when the compound is Formula (III), wherein $R_1$ is para-isopropyl phenyl; $R_2$ is hydrogen; $R_3$ is methyl; Y is $NR_5$ where $R_5$ is benzyl; and X is $NR_5$, wherein $R_5$ is hydrogen.

Encompassed in the formulations of the invention are the (+)-isomer, (−)-isomer, and mixtures of both isomers (e.g., racemic 1:1 mixtures) of all of the compounds of the invention unless such compounds are specifically excluded.

Variables, such as $R_1$-$R_7$, n, X and Y throughout the application are the same variables as previously defined unless stated to the contrary.

The term "alkyl" as used herein refers to a branched or unbranched saturated hydrocarbon group of 1 to 4, 1 to 8, or 1 to 20 carbon atoms, such as methyl, ethyl, n-propyl, isopropyl, n-butyl, isobutyl, t-butyl, pentyl, hexyl, heptyl, octyl, and the like. Examples of cycloalkyl groups include cyclopentyl and cyclohexyl.

The term "alkenyl" as used herein refers to a hydrocarbon group of 2 to 4, 2 to 8, or 2 to 20 carbon atoms and structural formula containing a carbon-carbon double bond.

The term "alkynyl" as used herein refers to a hydrocarbon group of 2 to 4, 2 to 8, or 2 to 20 carbon atoms and a structural formula containing a carbon-carbon triple bond.

The term "aryl" is defined as any carbon-based aromatic group including, but not limited to, phenyl, benzene, naphthalene, anthracene, phenanthrene, pyrene, and benzo[a] pyrene, etc.

The term "substituted aryl" is defined as an aryl group having at least one group attached to the aryl group that is not hydrogen. Examples of groups that can be attached to the aryl group include, but are not limited to, alkyl, alkynyl, alkenyl, aryl, heterocyclic, halide, nitro, amino, ester, ketone, aldehyde, hydroxy, carboxylic acid, alkoxy, cyano, alkoxy, thioalkyl, haloalkyl, hydroxyalkyl, alkylamino, dialkylamino, or acyl. In various embodiments, a substituent is bound to carbon 2, 3, 4, 5, or 6 of one of these moieties. Examples of alkoxy substituents include, but are not limited to, methoxy, ethoxy, and isopropoxy groups. Examples of acyl substituents include acetyl and benzoyl groups.

The term "aralkyl" is defined as an aryl group having an alkyl, alkynyl, or alkenyl group attached to the aryl group. An example of an aralkyl group is a benzyl group.

The term "heteroaryl" is defined as an aryl group that has at least one heteroatom such as nitrogen, sulfur, or oxygen incorporated within the ring of the aryl group.

The term "heteroalkyl" is defined as an alkyl group that has at least one heteroatom, such as nitrogen, sulfur, oxygen, or phosphate, incorporated within the alkyl group or attached to the alkyl group.

The compounds described herein may form salts with acids or bases, and such salts are included in the present invention. In one embodiment, the salts are pharmaceutically acceptable salts. The term "salts" embraces addition salts of free acids or free bases that are compounds of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification, or formulation of compounds of the invention.

Examples of the pharmaceutically acceptable salt of butanetap include acid addition salts prepared from a suitable acid. The suitable acid can be hydrobromic acid, hydrochloric acid, hydroiodic acid, sulfuric acid, carbonic acid, nitric acid, phosphoric acid, tetrafluoroboronic acid, perchloric acid, 1-hydroxy-2-naphthoic acid, 2,2-dichloroacetic acid, methanesulfonic acid, trifluoromethanesulfonic acid, 2-hydroxyethanesulfonic acid, benzenesulfonic acid, p-toluenesulfonic acid, cyclohexylaminosulfonic acid, 2-oxoglutaric acid, 4-acetamidobenzoic acid, acetic acid, phenylacetic acid, propionic acid, formic acid, succinic acid, glycolic acid, gluconic acid, malic acid, lactic acid, tartaric acid, citric acid, glucuronic acid, ascorbic acid, maleic acid, fumaric acid, pyruvic acid, aspartic acid, glutamic acid, benzoic acid, 4-hydroxybenzoic acid, anthranilic acid, 4-hydroxybenzoic acid, mandelic acid, pamoic acid, pantothenic acid, sulfanilic acid, stearic acid, alginic acid, p-hydroxybutyric acid, salicylic acid, galactaric acid and galacturonic acid. Preferably, the pharmaceutically acceptable salt is butanetap tartrate, i.e., the acid addition salt of tartaric acid.

Suitable pharmaceutically acceptable base addition salts of compounds of the invention include, for example, metallic salts including alkali metal, alkaline earth metal and transition metal salts such as, for example, calcium, magnesium, potassium, sodium, and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N methylglucamine) and procaine. Examples of pharmaceutically unacceptable base addition salts include lithium salts and cyanate salts. All of these salts may be prepared from the corresponding compound by reacting, for example, the appropriate acid or base.

Administration and Dosing

In the methods of the invention, butanetap, its analogs, metabolites, or a pharmaceutically acceptable salt thereof can be administered parenterally or enterally. Examples of the route of administration of butanetap or an analog, metabolite, or pharmaceutically acceptable salt thereof are intravenous, intraocular, intramuscular, subcutaneous, topical, oral, sublingual, and buccal. Preferably, for purposes of the present invention, butanetap is administered orally.

In the present invention, butanetap, or a pharmaceutically acceptable salt of butanetap, can be administered once, twice, three times, or four times daily. Butanetap is preferably administered on a once-a-day basis. Depending on the route of administration, butanetap is administered in different dose ranges.

In certain embodiments (butanetap) is administered orally in an amount from about 1 mg to about 120 mg, preferably on a once-a-day basis. In certain preferred embodiments, butanetap is administered in an amount from about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, and numbers in between these numbers, and all further integers to about 120 mg, preferably on a once a day basis. In certain preferred embodiments, butanetap is administered orally in a dose from about 10 mg to about 80 mg. In other embodiments, the butanetap dose is administered intravenously in an amount from about 0.1 to about 25 mg/day. In other preferred embodiments, the butanetap dose is administered intraperitoneally/intramuscularly (IP/IM) in a dose from about 0.3 to about 70 mg/day. Doses for humans believed to be efficacious and safe are set forth in Table 1 below for oral, IP/IM, and IV routes of administration:

TABLE 1

| ORAL Human Efficacious and Safe Dose mg/day | IP/IM Human Efficacious and Safe Dose mg/day | IV Human Efficacious and Safe Dose mg/day |
|---|---|---|
| | | 0.1 |
| | 0.3 | 0.3 |
| 1.0 | 1.0 | 1.0 |
| 4.9 | 4.9 | 4.9 |
| 10.0 | 10.0 | 10.0 |
| 11.2 | 11.2 | 11.2 |
| 14.7 | 14.7 | 14.7 |
| 16.1 | 16.1 | 16.1 |
| 20.3 | 20.3 | 20.3 |
| 23.8 | 23.8 | 23.8 |
| 39.9 | 39.9 | |
| 70.0 | 70.0 | |
| 79.8 | | |
| 119.7 | | |
| 1 to 120 | 0.3 to 70 | 0.1 to 25 |

In certain embodiments of each of the methods described above, the oral pharmaceutical composition includes from about 1 mg to about 120 mg butanetap or a pharmaceutically acceptable salt thereof, the IP/IM pharmaceutical composition includes from about 0.3 to about 70 mg butanetap or a pharmaceutically acceptable salt thereof, and the intravenous (IV) pharmaceutical formulation includes from about 0.1 to about 25 mg butanetap or a pharmaceutically acceptable salt thereof.

In general, the dose of butanetap preferred to be administered to healthy human patients is a tolerable dose, i.e., a dose that does not cause untoward side effects in a majority of human patient, which dose is also effective for prophylactic treatment of the healthy human(s) with respect to, e.g., neurodegenerative diseases, cancer, cardiovascular homeostasis, diseases or conditions of vital organs, cardiovascular disease, and the like.

In certain preferred embodiments of the methods described herein, peak plasma circulating levels of butanetap in humans range, e.g., from about 1 ng/mL to about 380 ng/mL, in certain embodiments from about 2 ng/mL to about 20 ng/mL, and more preferably from about 3.7 ng/mL to about 120 ng/mL. In certain preferred embodiments, the peak plasma circulating level is reached within about 6 hours after administration of butanetap to humans. In certain embodiments, the peak plasma circulating level is reached within about 3 hours after administration of butanetap to the humans. In certain embodiments, the plasma circulating level of butanetap is equal to or greater than about 1 ng/mL, 2 ng/mL, 3 ng/mL, 4 ng/mL, 5 ng/mL, 6 ng/mL, 7 ng/mL, 8 ng/mL, 9 ng/mL, 10 ng/mL, 11 ng/mL, 12 ng/mL, 13 ng/mL, 14 mg/mL, 15 ng/mL, 16 ng/mL, 17 ng/mL, 18 ng/mL, 19 ng/mL, or 20 ng/mL for at least 9 hours, and preferably for at least 12 hours, after administration of butanetap to humans. In certain embodiments, the steady-state plasma concentration of butanetap is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 11, 112, 113, 114, 115, 116, 117, 118, 119 or 120 ng/mL. In certain embodiments, the half-life of butanetap in cerebrospinal fluid after administering is about 12 hours, and the half-life of butanetap in plasma after administering is about 5 hours. In certain embodiments, the administration of butanetap to humans results in a brain level of butanetap that range from about 4 to about 10 times the plasma level of butanetap in those patients. In certain embodiments, the concentration of butanetap in the brain of humans is from about 8 ng/g to about 3040 ng/g, in certain embodiments from about 30 ng/g to about 960 ng/g. Table 2 provides plasma levels for humans and brain levels for humans as calculated and extrapolated from animal (mice data):

TABLE 2

| Dose mg/kg | mg dose for 70 kg | Plasma levels in mice n/ml | Plasma levels in human ng/ml | Brain levels in mice ng/gram | Brain levels in humans ng/gram |
|---|---|---|---|---|---|
| 0.014 | 1.0 | 0 | 1 | 0 | 8 |
| 0.07 | 4.9 | 0 | 2 | 0 | 16 |
| 0.143 | 10.0 | 0 | 3.7 | 0 | 29.6 |
| 0.16 | 11.2 | 0 | 5.7 | 0 | 45.6 |
| 0.21 | 14.7 | 0 | 11.5 | 0 | 92 |
| 0.23 | 16.1 | 0 | 12.9 | 0 | 103.2 |
| 0.29 | 20.3 | 0 | 14 | 0 | 112 |
| 0.34 | 23.8 | 0 | 20 | 0 | 160 |
| 0.57 | 39.9 | 0 | 42 | 0 | 336 |
| 1 | 70.0 | 2 | 90 | 16 | 720 |
| 1.14 | 79.8 | 2.1 | 120 | 16.8 | 960 |
| 1.71 | 119.7 | 0 | 200 | 0 | 1600 |
| 2.13 | 149.1 | 3.9 | 240 | 31.2 | 1920 |
| 2.29 | 160.3 | 0 | 380 | 0 | 3040 |
| 3 | | 6 | | 48 | |
| 5 | | 10 | | 80 | |
| 10 | | 20 | | 160 | |
| 20 | | 50 | | 400 | |
| 30 | | 100 | | 800 | |
| 40 | | 150 | | 1200 | |
| 50 | | 210 | | 1680 | |
| 60 | | 300 | | 2400 | |
| 80 | | 600 | | 4800 | |
| 100 | | 1000 | | 8000 | |

In certain embodiments, the methods of the present invention further include administering a second pharmaceutically active agent for the purpose of prophylactically treating the human to prevent, slow or delay a disease state or condition as described herein. In such embodiments, the invention is further is directed to a packaged pharmaceutical composition comprising a container holding a therapeutically effective amount of butanetap or other compound in accordance with the invention, alone or in combination with a second pharmaceutical agent; and instructions for using the composition to treat, prevent, or reduce one or more symptoms of a disease in a subject.

Pharmaceutical Compositions and Therapies

Administration of a compound useful within the invention may be achieved in a number of different ways, using methods known in the art. The therapeutic and prophylactic methods of the invention thus encompass the use of pharmaceutical compositions comprising the compounds useful within the invention to practice the methods of the invention. The pharmaceutical compositions useful for practicing the invention may be administered to deliver a dose of 1 ng/kg/day to 100 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Although the description of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Typically, dosages which may be administered in a method of the invention to an animal, preferably a human, range in amount from 0.5 μg to about 50 mg per kilogram of body weight of the animal. While the precise dosage administered will vary depending upon any number of factors, including but not limited to, the type of animal and type of disease state being treated, the age of the animal and the route of administration, the dosage of the compound will preferably vary from about 1 μg to about 10 mg per kilogram of body weight of the animal. More preferably, the dosage will vary from about 3 μg to about 1 mg per kilogram of body weight of the animal.

Pharmaceutical compositions that are useful in the methods of the invention may be prepared, packaged, or sold in formulations suitable for oral, parenteral, topical, buccal, or another route of administration. Other contemplated formulations include projected nanoparticles, liposomal preparations, resealed erythrocytes containing the active ingredient, and immunologically based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The composition of the invention may consist of the active ingredient alone, in a form suitable for administration to a (human) subject or patient, or the composition may comprise at least one active ingredient and one or more pharmaceutically acceptable excipients.

In one embodiment, the compositions of the invention are formulated using one or more pharmaceutically acceptable carriers. Pharmaceutically acceptable carriers that are useful, include, but are not limited to, glycerol, water, saline, ethanol, and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey). The carrier may be a solvent or dispersion medium containing, for example, water, ethanol, polyol (for example, glycerol, propylene glycol, and liquid polyethylene glycol, and the like), suitable mixtures thereof, and vegetable oils.

Formulations may be employed in admixtures with conventional excipients, i.e., pharmaceutically acceptable organic or inorganic carrier substances suitable for oral, vaginal, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, PA), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. A particularly preferred preservative is a combination of about 0.5% to 2.0% benzyl alcohol and 0.05% to 0.5% sorbic acid.

The composition preferably includes an antioxidant and a chelating agent that inhibits the degradation of the compound. Preferred antioxidants for some compounds are BHT, BHA, alpha-tocopherol and ascorbic acid in the preferred range of about 0.01% to 0.3% and more preferably BHT in the range of 0.03% to 0.1% by weight by total weight of the composition. Preferably, the chelating agent is present in an amount of from 0.01% to 0.5% by weight by total weight of the composition. Particularly preferred chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing, or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, and acacia. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

Controlled- or sustained-release formulations of a composition of the invention may be made using conventional technology, in addition to the disclosure set forth elsewhere herein. In some cases, the dosage forms to be used can be provided as slow or controlled release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the compositions of the invention.

Controlled release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, nanoparticles, or microspheres or a combination thereof that facilitates the controlled-release of the active ingredient.

Routes of administration of any of the compositions of the invention include oral, nasal, rectal, parenteral, sublingual, transdermal, transmucosal (e.g., sublingual, lingual, (trans) buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

For oral administration, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more inert, non-toxic pharmaceutically excipients. Such excipients include, for example an inert diluent such as lactose; granulating and disintegrating agents such as cornstarch; binding agents such as starch; and lubricating agents such as magnesium stearate. The oral compositions of the invention in the form of tablets or capsules prepared by conventional means with pharmaceutically acceptable excipients such as binding agents; fillers; lubricants; disintegrates; or wetting agents.

Tablets may be non-coated, or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation. For oral administration, if desired, the tablets may be coated using suitable methods and coating materials such as OPADRY® film coating systems available from Colorcon, West Point, Pa. (e.g., OPADRY® OY Type, OYC Type, Organic Enteric OY-P Type, Aqueous Enteric OY-A Type, OY-PM Type and OPADRY® White, 32K18400).

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin. Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid preparation for oral administration may be in the form of solutions, syrups, or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface-active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface-active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intrasternal injection, intratumoral, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen free water) prior to parenteral administration of the reconstituted composition.

A pharmaceutical composition of the invention may be prepared, packaged, or sold in a formulation suitable for topical administration. There are several advantages to delivering compounds, including drugs or other therapeutic agents, into the skin (dermal drug delivery) or into the body through the skin (transdermal drug delivery). Transdermal compound delivery offers an attractive alternative to injections and oral medications.

Additional dosage forms of this invention include dosage forms as described in U.S. Pat. Nos. 6,340,475; 6,488,962; 6,451,808; 5,972,389; 5,582,837 and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

DETAILED DESCRIPTION OF PREFERRED EMBODIMENTS

The following examples further illustrate aspects of the present invention. They are provided for the purpose of illustration only, and the invention is not limited to these Examples, but rather encompasses all variations that are evident as a result of the teachings provided herein.

Example 1

Three Phase I clinical studies have established butanetap's safety. The pharmacokinetic analyses have demonstrated that the small lipophilic molecule readily enters the brain where its concentration is about 8 times higher than in plasma. Importantly, butanetap normalized levels of APP, Tau, and αSYN in the cerebrospinal fluid (CSF) of MCI subjects at a dose of 4×60 mg/day. butanetap had a >12 h half-life in CSF of MCI subjects, and its effect in lowering these neurotoxic proteins and inflammation extended throughout the 12 h sampling period after the last dose (Maccecchini, et al., "*Butanetap* (*Posiphen*) *as a Candidate Drug to Lower CSF Amyloid Precursor Protein, Amyloid-β Peptide and r Levels: Target Engagement, Tolerability and Pharmacokinetics in Humans*", J. Neurosurg. Psychiatry 2012; 83:894-902). Therefore, we conclude that a much lower single daily butanetap dose would be effective in the proposed study. In fact, much lower doses were studied in a double Alzheimer/Parkinson phase 2 study that was conducted and completed in 2021 (effective IND #72,654). The double phase 2 clinical trial recruited 14 AD and 54 PD patients and treated them over 25 with a once daily dose of buntanetap. The 14 AD patients receive either 80 mg QD or placebo, whereas the 54 PD patients received 5, 10 20, 40 80 mg QD or placebo. In a nutshell the data shows that in AD and in PD patients (a) buntanetap crossed the blood brain barrier, (b) reduced neurotoxic protein biomarkers, (c) reduced inflammatory markers, (d) improved axonal and synaptic function, and most importantly improved the affected function in both patient populations. In AD patients buntanetap improved cognition as measured by ADAS-Cog11 and WAIS coding speed (achieving statistical significance versus baseline at 80 mg dose but not placebo). In PD patients it improved at all doses motor function as measured by MDS-UPDRS (Part II, III, IV and total) with the maximum improvement for 10 & 20 mg and improved WAIS speed and accuracy (achieving statistical significance versus placebo in the 5 mg, 20 mg and 80 mg dose arms [$p<0.05$] of the broader study population [n=54] with the total for all doses also reporting statistically significant improvement [$p<0.001$])[19, 32]. The data demonstrates the potential benefits of reducing the overexpression of neurotoxic aggregating proteins on inflammation, axonal and synaptic function, and cognitive and functional health. We expect a larger sample population will allow buntanetap to fully demonstrate statistically significant cognitive and functional improvement resulting from the normalization of toxic protein levels in the next planned AD study as has already been demonstrated for PD (where a phase 3 trial is pending).

Butanetap's effect on neurotoxic proteins. The drug lowers levels of APP in vitro in neuroblastoma cells (Mikillineni et al: Parkinson's Disease; Volume 2012, Article ID 142372, 13 pages. *The Anticholinesterase Phenserine and Its Enantiomer Butanetap (Posiphen) as 5′ Untranslated-Region-Directed Translation Blockers of the Parkinson's Alpha Synuclein Expression*). It also lowers levels of APP and all its fragments in APP/PS1 transgenic mice (A. F. Teich, et al., *Alzheimer;s & Dementia: Translational Research & Clinical Interventions* 4 (2018) 37-45). Butanetap also lowers tau in vitro (Peter Davies Laboratory, Hofstra University, unpublished observation) and in vivo in Human tau mice (Peter Davies Laboratory, Hofstra University, unpublished observation). Butanetap further lowers aSYN in vitro in neuroblastoma cells and in vivo in transgenic Parkinson's animals in the brain and in the gut (Kuo et. al. Am J Neurodegener Dis 2019; 8(1):1-15 www.AJND.us/ISSN: 216 591X/AJND0086080*: Translational inhibition of* α*-synuclein by Butanetap (Posiphen) normalizes distal colon motility in transgenic Parkinson mice*).

Butanetap's efficacy in treating neurodegeneration in animal models: Restored memory and learning in an APP/PS1 transgenic (tg) mouse model of AD; Restored memory and learning in a Ts65dn mouse model of Down syndrome (DS) [W. Mobley, UCSD, submitted 2020]; Preserved the retina in acute glaucoma [J Sundstrom; Hershey Medical School]; Restored colonic motility in a human SNCAA53T tg mouse model of PD (Kuo et. al., Am J Neurodegener Dis 2019; 8(1):1-15 www.AJND.us/ISSN:216 591X/AJND0086080*: Translational inhibition of* α*-synuclein by Butanetap (Posiphen) normalizes distal colon motility in transgenic Parkinson mice*); Preserved memory and learning in traumatic brain injury rats (M-F Chesselet, submitted 2020).

Butanetap's reversal of the neurotoxic cascade: Butanetap's mechanism of action is related to APP, Tau, and aSYN expression being regulated by RP1 and by iron and the way these proteins contribute to neurodegeneration by accumulating as toxic aggregates that impair axonal transport and synaptic transmission, causing inflammation, and, finally, leading to nerve cell death (as described previously). By reducing APP, Tau, and αSYN levels, butanetap treatment prevented this toxic cascade. In support of this hypothesis, it has been shown that butanetap: Normalized anterograde and retrograde vesicle transport in fully differentiated Down syndrome nerve cells [W. Mobley; USCD]; Normalized impaired synaptic transmission in rat striatum after traumatic brain injury (TBI) [M-F Chesselet; UCLA] and hippocampus of APP/PS1 tg mice; lowered inflammation in human CSF of MCI subjects and in the rat brain after TBI; protected nerve cells in rat substantia Ingra after TBI and in a rat acute glaucoma model (J Sundstrom; Hershey Medical School).

The AD field has been dominated by approaches to prevent APP processing or remove Aβ in one of its many forms. These are downstream targets; butanetap prevents the translational synthesis of the two main proteins involved in AD—APP and tau—and hence should remove all the downstream consequences produced by these proteins. Similarly, the PD field mostly focuses on inhibiting accumulation of αSYN aggregates and the effect of other proteins in this pathway, including LRRK or Parkin. Again, butanetap prevents the synthesis of αSYN and thus it should stop the pathological cascade at the first step. Our data indicate that by normalizing the levels APP/As, Tau/phospho-Tau, and αSYN, butanetap normalizes axonal transport, lowers inflammation, and protects nerve cells from dying. (Mobley 2020, submitted for publication; Chesselet 2020, submitted for publication)

Example 2

APP

A. FIG. 1, APP in vitro. shows that butanetap lowers APP in vitro in a dose-dependent manner in SH-SY-5Y human neuroblastoma cells. On the left is a Western blot showing butanetap inhibition of APP in relation to Actin standard at concentrations of 0, 0.1, 1, 5 and 10 μM and a graph showing the same data plotted for statistical analysis purposes.

Figure 2:
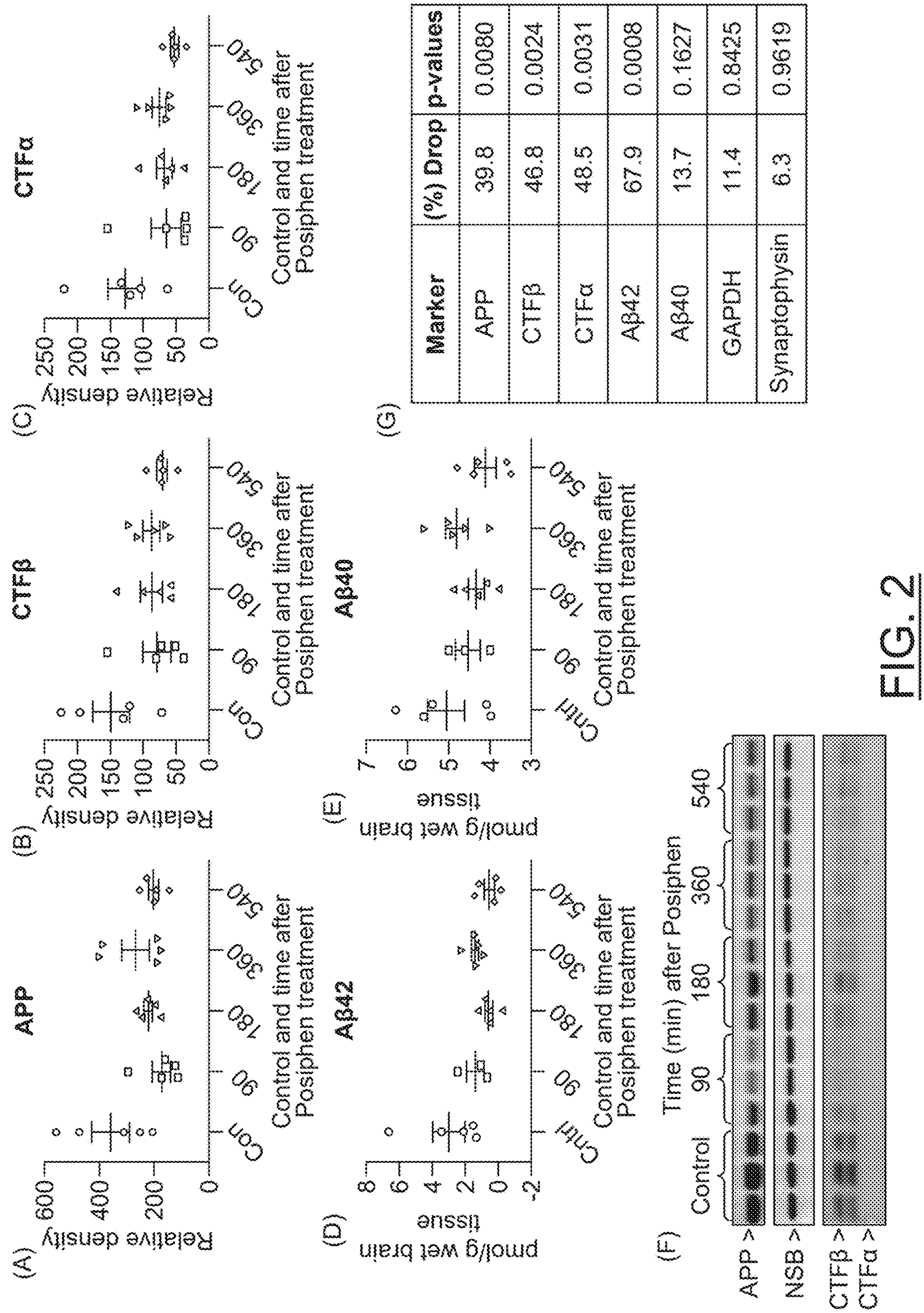
FIG. 2 is a Table, collection of graphs and a Western blot showing that butanetap treatment of APP/PS1 transgenic AD mice reduced APP and its fragments in hippocampus.

B. FIG. 2, APP in vivo. This study was conducted to demonstrate the effect of butanetap in inhibiting the translation of APP and its fragments in an AD model in vivo. The Table in FIG. 2 shows that butanetap treatment of APP/PS1 transgenic AD mice reduced APP and its fragments in hippocampus. GAPDH and Synaptophysin were loading controls. FIG. 2 also includes a collection of graphs showing relative density of APP plotted against control and time after butanetap treatment; relative density of CTFβ plotted against control and time after butanetap treatment; relative density of CTFα plotted against control and time after butanetap treatment; Aβ42 levels in brain tissue plotted against control and time after butanetap treatment; and Aβ40 levels in brain tissue plotted against control and time after butanetap treatment. Finally, FIG. 2 also includes a Western blot showing levels of APP, NSB, CTFβ, and CTFα after butanetap treatment over time (minutes). In APP/PS1 mice expressing human mutations associated with familial AD, the data show that butanetap treatment reduced APP and all related peptides in hippocampus for at least 9 hours after the last dose.

Example 3

TAU

Figure 3:
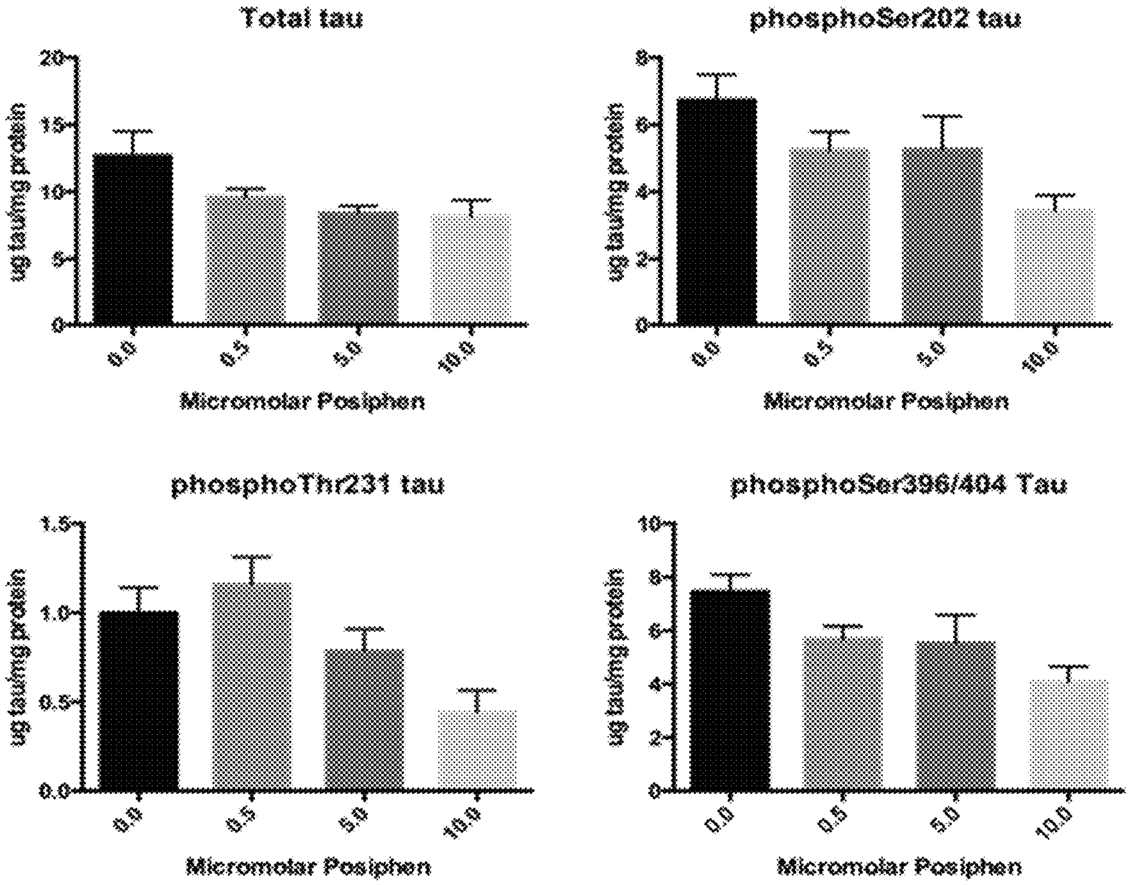
FIG. 3 is graphs showing that butanetap reduces Tau expression in vitro in transgenic neo-natal human Tau mice cells.

A. FIG. 3 Tau in vitro. butanetap reduces Tau expression in vitro in transgenic neo-natal human Tau mice cells. The cells were treated for 4 days with butanetap harvested, solubilized, and tested with antibodies against Tau and phospho-Tau.

Figure 4:
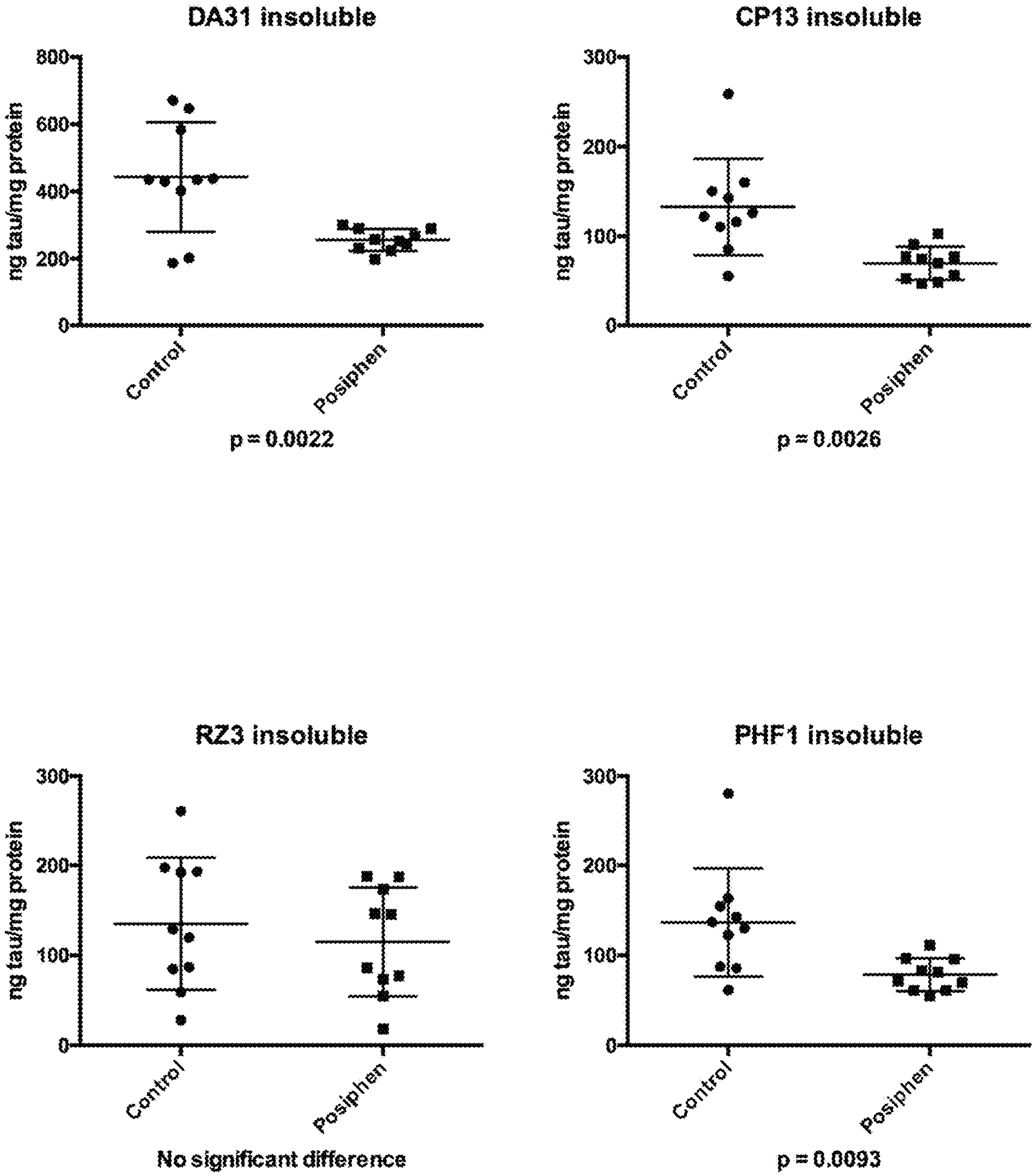
FIG. 4 is graphs showing that butanetap treatment in vivo produced a significant reduction in the amount of insoluble tau in mice.

B. FIG. 4, Tau in vivo. It shows the results of a small pilot study with butanetap treatment of hTau mice (N=10 per group), adding the butanetap to the mouse chow. After 6 weeks, mice were killed and the total and insoluble (aggregated) tau was measured. Butanetap produced a significant reduction in the amount of insoluble tau with three of the 4 ELISA assays used. Precipitated tau corresponds to tangles in the brain.

Example 4 aSYN

Figure 5:
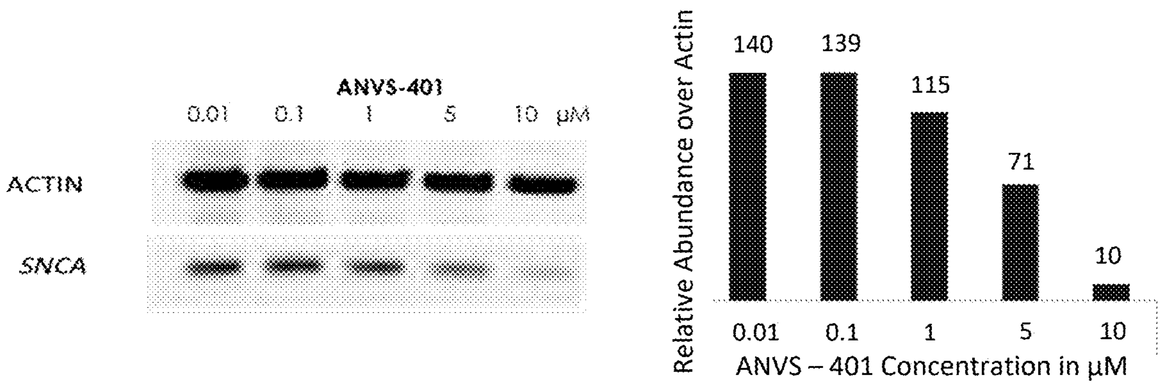
FIG. 5 is a Western blot and a graph showing that butanetap lowers aSYN in vitro in a dose-dependent manner in SH-SY-5Y human neuroblastoma cells.

A. FIG. 5, alpha-synuclein in vitro. This figure shows that butanetap lowers aSYN in vitro in a dose-dependent manner in SH-SY-5Y human neuroblastoma cells. On the left is a Western blot showing butanetap inhibition of aSYN in relation to Actin standard at concentrations of 0, 0.1, 1, 5 and 10 μM and on the right a graph showing the same data plotted for statistical analysis purposes.

Figure 6:
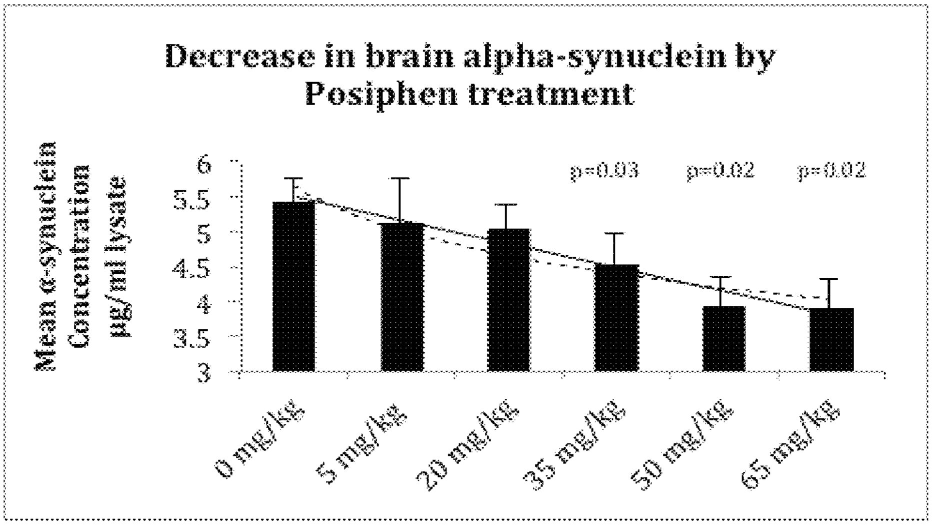
FIG. 6 is a graph showing that butanetap reduced aSYN in the brain of animals in vivo.

B. FIG. 6, alpha-synuclein brain in vivo. The figure shows that 50 and 65 mg/kg for 21 days reduced αSYN in the brain. The animals were only treated for 2 weeks, so in brain it takes butanetap only 2 weeks to lower levels of alpha-synuclein.

Figure 7A:
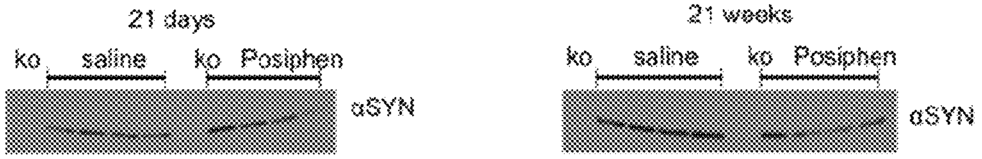
FIG. 7A and FIG. 7B are graphs showing that butanetap treatment significantly reduced alpha-synuclein levels in vivo in mice.
Figure 7B:
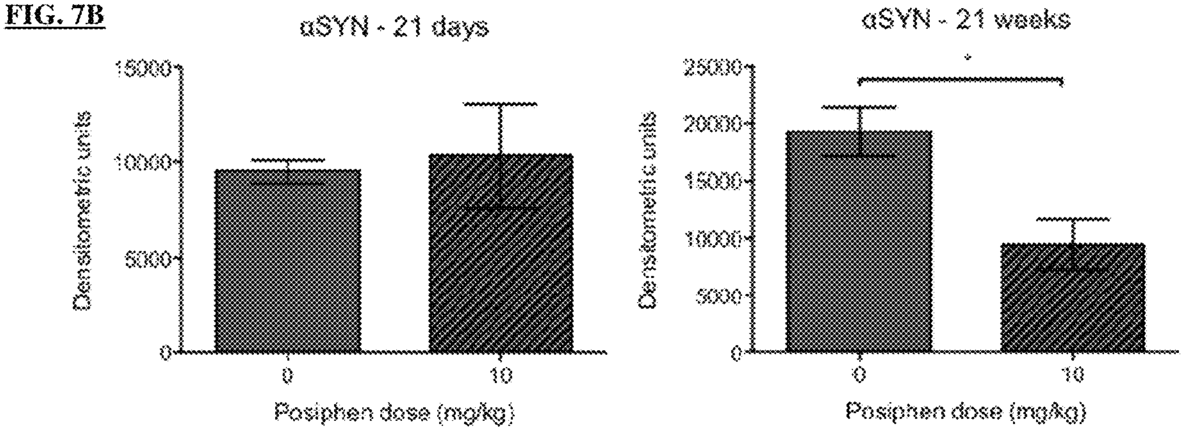

C. FIG. 7, alpha-synuclein in gut in vivo. Gut levels of aSYN following treatment of PD A53T mice with 10 mg/kg for 21 weeks and 21 days reduced αSYN levels in the gut as shown by Western Blot. Quantization of the alpha-synuclein Western blots showed that at 21 weeks, but not at 21 days, butanetap treatment significantly reduced alpha-synuclein levels by 50.6%—$p<0.05$.

In summary, Example 4 shows that butanetap inhibits alpha-synuclein in tissue culture cells, in the brain of mice as well as in the gut of the same mice. Butanetap inhibits alpha-synuclein in the central and peripheral nervous system.

Example 5

Human Data

Figures 8, 9:
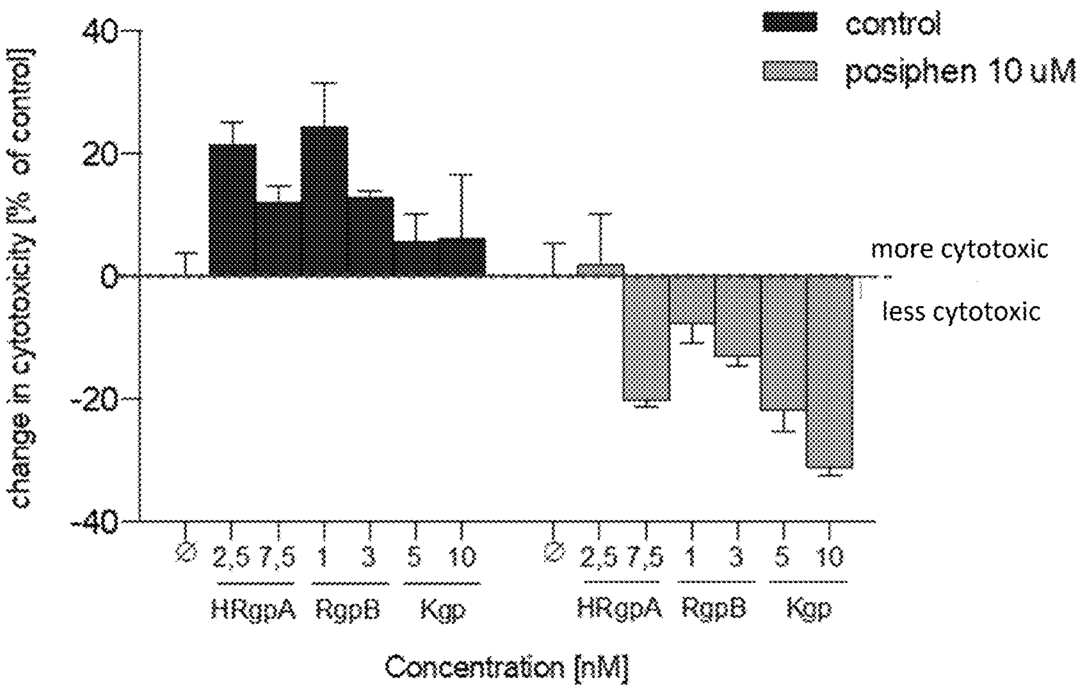
FIG. 8 is a table showing the reduction of APP/Abeta, tau/phospho-tau and alpha-synuclein in the spinal fluid of mildly cognitive impaired patients.
FIG. 9 is a graph showing mouse astrocytes infected for 48 hours with all three gingivalis proteases (gingipains HRgpA, RgpB, and Kgp) where the change in cytotoxicity (% control) is plotted against concentration [nM] of the three gingivalis proteases, are killed in a dose dependent fashion. It is believed that butanetap has no impact on the microglia or neuroblastoma survival in the presence of gingipains.

FIG. 8 is a study of subjects with MCI for early proof of mechanism (POM) using a well-tolerated dose of butanetap. Before and after 10 days of butanetap administration to the MCI subjects, plasma and cerebrospinal fluid (CSF) samples were obtained for analysis of levels of secreted (s) APPα and APPβ, and Aβ42, Tau (total and phosphorylated), and inflammatory markers. FIG. 8 shows the reduction of APP/As, tau/phosphor-tau and alpha-synuclein in the spinal fluid of mildly cognitive impaired patients. In this study, butanetap normalized these aggregating proteins in CSF of MCI subjects in accordance with the data seen in animals.

Example 6

Once the brain is infected with *P. gingivalis*, two proteases attack and kill nerve cells. *P. gingivalis* and its associated proteases infect astrocytes, who in turn release neurotoxic proteins that kill nerve cells and butanetap (butanetap) protects the brain from dying. This is illustrated by the following.

Immortalized Mouse Astrocytes—SV40T (IMA2.1), immortalized Mouse Microglia (SIM-A9) and immortalized neuroblastoma (SH-SY5Y) cells were infected for 48 hours with gingipains HRgpA and RgpB (arginine gingipains), and Kgp (lysine-specific cysteine proteinase—Lys-gingipain, KGP). After 48 hours the cells were assessed for viability with the AlamarBlue assay and the percentage of dead or alive cells versus control was plotted. We found that microglia and neuroblastoma cell lines are not affected by *P. gingivalis* infection as both are quite resistant to gingipains. As expected, since neither are dying, buntanetap at concentrations between 1 and 10 nM. These concentrations are comparable to the concentrations needed to lower the levels of neurotoxic aggregating proteins in vitro shown in examples 1 to 4. Therefore, we expect the efficacious buntanetap dose to fight *P. gingivalis* infection to be the same as to treat Alzheimer's and Parkinson's disease has no impact on the microglia or neuroblastoma survival in the presence of gingipains. However, all gingipains (HRgpA, RgpB and Kgp) kill astrocytes in a dose dependent fashion. These results are depicted in FIG. 9, which is a graph showing mouse astrocytes infected for 48 hours with all three gingivalis proteases (gingipains HRgpA, RgpB, and Kgp) where the change in cytotoxicity (% control) is plotted against concentration [nM] of the three gingivalis proteases, showing that butanetap has no impact on the microglia or neuroblastoma survival in the presence of gingipains.

Example 7

Example 7 shows that retesting of the gingipain effect on astroglia at much lower concentrations showed that buntanetap (butanetap) protects astrocytes at very low concentrations.

In Example 7, at the concentration of 1 nM gingipain infected cells were completely protected from the enzyme while only around 20% of the control cells survived.

Figure 10:
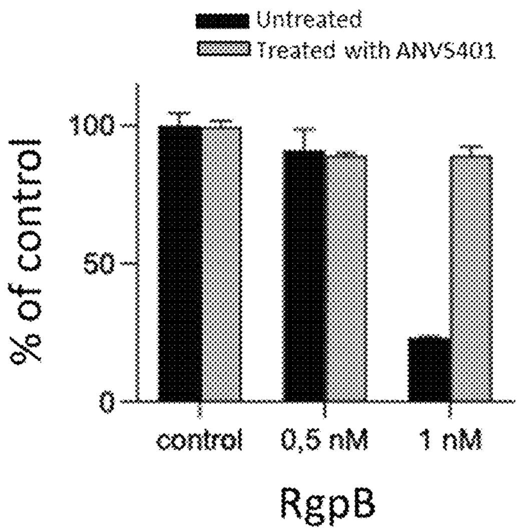
FIG. 10 show the results of retesting of the gingipain effect on astroglia at much lower concentrations. It shows the change in cytotoxicity (% control) is plotted against concentration [nM] and that at 1 nM gingipain infected cells were completely protected from the enzyme while only about 20% of the control cells survived.

FIG. 10 show the results of retesting of the gingipain effect on astroglia at much lower concentrations. It shows the change in cytotoxicity (% control) is plotted against concentration [nM] and that at 1 nM gingipain infected cells were completely protected from the enzyme while only about 20% of the control cells survived.

Example 8

Figure 11:
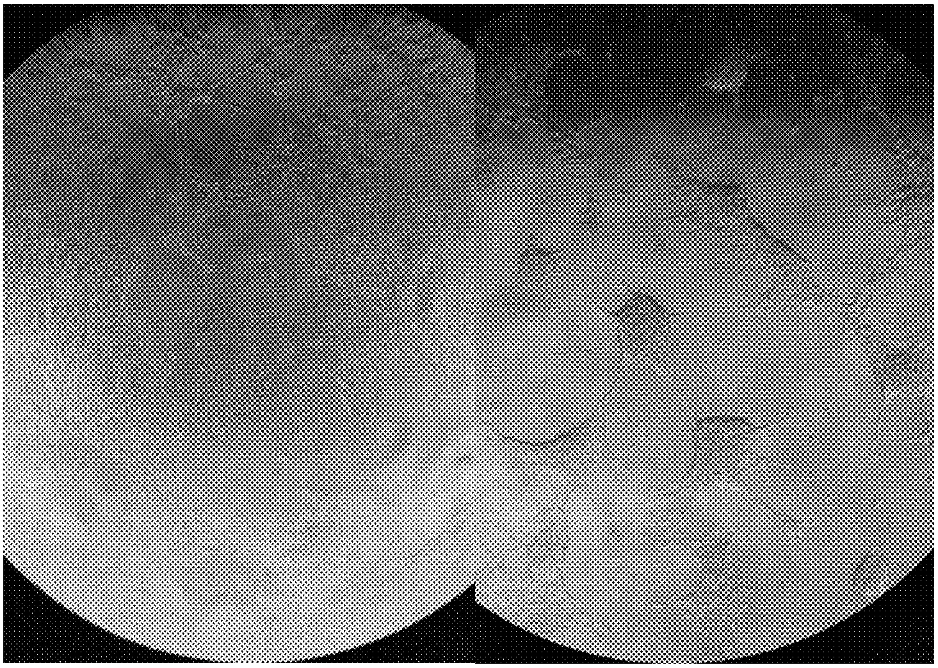
FIG. 11 is a photograph showing that infection neuroblastoma cells (SH-SY5Y) demonstrate cell aggregation after exposure for 24 hours to RgpB (10 ug/ml), Kgp (10 ug/ml), or both.

Example 8 demonstrates that the addition of butanetap blocks the gingipain-induced cell aggregation, and the cells look healthy and normal. This is shown in FIG. 11, which [1] is a photograph showing that infected neuroblastoma cells (SH-SY5Y) demonstrate cell aggregation after exposure for 24 hours to RgpB (10 ug/ml), Kgp (10 ug/ml), or both.

Table 3 below provides dose that are useful in humans and mice. The doses are provided in mg/kg; mg dose for a 70 kg human; plasma levels in mice and humans (ng/ml); plasma levels in humans (nM); brain levels in mice and humans (ng/gram); oral human efficacious and safe dose (mg/day); IP/P human efficacious and safe dose (mg/day); and IV human efficacious and safe dose (mg/day). It is believed that efficacious IP/IM dosing is in the middle of these ranges (e.g., about 60 mg/day based on the oral dose; about 35 mg/day based on the IP/IP human dose; and about 12.5 mg/day based on the IV dose). Between about 120 mg/day and 200 mg/day, butanetap turns toxic. The dose of 1 nM Butanetap was found to be efficacious, as was the (extrapolated) plasma level of about 10 to about 10,000 nM in tissue culture.

TABLE 3

| Dose mg/kg | mg dose for 70 kg | Plasma levels in mice ng/ml | Plasma levels in human ng/ml | Plasma levels in humans nM | Brain levels in mice ng/gram | Brain levels in humans ng/gram | ORAL Human Efficacious and Safe Dose mg/day | IP/IP Human Efficacious and Safe Dose mg/day | IV Human Efficacious and Safe Dose mg/day |
|---|---|---|---|---|---|---|---|---|---|
| | | | | | | | | | 0.1 |
| | | | | | | | | 0.3 | 0.3 |
| 0.014 | 1.0 | 0 | 1 | 3 | 0 | 8 | 1.0 | 1.0 | 1.0 |
| 0.07 | 4.9 | 0 | 2 | 6 | 0 | 16 | 4.9 | 4.9 | 4.9 |
| 0.143 | 10.0 | 0 | 3.7 | 10 | 0 | 29.6 | 10.0 | 10.0 | 10.0 |
| 0.16 | 11.2 | 0 | 5.7 | 17 | 0 | 45.6 | 11.2 | 11.2 | 11.2 |
| 0.21 | 14.7 | 0 | 11.5 | 32 | 0 | 92 | 14.7 | 14.7 | 14.7 |
| 0.23 | 16.1 | 0 | 12.9 | 38 | 0 | 103.2 | 16.1 | 16.1 | 16.1 |
| 0.29 | 20.3 | 0 | 14 | 41 | 0 | 112 | 20.3 | 20.3 | 20.3 |
| 0.34 | 23.8 | 0 | 20 | 58 | 0 | 160 | 23.8 | 23.8 | 23.8 |
| 0.57 | 39.9 | 0 | 42 | 123 | 0 | 336 | 39.9 | 39.9 | |
| 1 | 70.0 | 2 | 90 | 264 | 16 | 720 | 70.0 | 70.0 | |
| 1.14 | 79.8 | 2.1 | 120 | 352 | 16.8 | 960 | 79.8 | | |
| 1.71 | 119.7 | 0 | 200 | | 0 | 1600 | 119.7 | | |
| 2.13 | 149.1 | 3.9 | 240 | | 31.2 | 1920 | | | |
| 2.29 | 160.3 | 0 | 380 | | 0 | 3040 | 1 to 120 | 0.3 to 70 | 0.1 to 25 |
| 3 | | 6 | | | 48 | | | | |
| 5 | | 10 | | | 80 | | | | |
| 10 | | 20 | | | 160 | | | | |
| 20 | | 50 | | | 400 | | | | |
| 30 | | 100 | | | 800 | | | | |
| 40 | | 150 | | | 1200 | | | | |
| 50 | | 210 | | | 1680 | | | | |
| 60 | | 300 | | | 2400 | | | | |
| 80 | | 600 | | | 4800 | | | | |
| 100 | | 1000 | | | 8000 | | | | |

CONCLUSION

The data presented in these Examples is relevant to the presently claimed invention because infections, whether viral, bacterial or fungal, all cause an increase in APP/Abeta and tau/phospho-tau, and butanetap is shown to lower the levels of these two neurotoxic proteins. Therefore, butanetap stops or inhibits the toxic cascade leading through axonal transport, to inflammation and to loss of nerve cells and therefore loss of function.

While the invention has been disclosed with reference to specific embodiments, it is apparent that other embodiments and variations of this invention may be devised by others skilled in the art without departing from the true spirit and scope of the invention. All patents and publications cited herein are incorporated by reference in their entirety. The appended claims are intended to be construed to include all such embodiments and equivalent variations.

What is claimed is:

1. A method for inhibiting or treating neurological damage in a human who is infected by a bacterium that secretes gingipains, comprising administering to the human a therapeutically effective amount of buntanetap of Formula (IV), (IV)

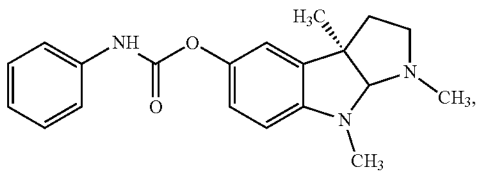

or a pharmaceutically acceptable salt thereof.

2. The method of claim 1, wherein the therapeutically effective amount is administered orally once-a-day.

3. The method of claim 2, wherein the therapeutically effective amount is from about 2 mg to about 80 mg.

4. The method of claim 1, wherein the buntanetap or the pharmaceutically acceptable salt thereof is administered via a route selected from the group consisting of orally, parenterally, sublingually, via suppository, nasally, topically, transdermally, and via implant under a skin.

5. The method of claim 1, wherein the buntanetap or the pharmaceutically acceptable salt thereof is administered to the human prior to the infection directly or indirectly causing a neurological disorder or a neurodegenerative disease.

6. The method of claim 1, wherein the buntanetap or the pharmaceutically acceptable salt thereof is administered to the human until the human is no longer infected.

7. The method of claim 1, wherein the human experiences neurological damage and the buntanetap or the pharmaceutically acceptable salt thereof is administered to the human until the human is no longer infected and neurological damage in the human has been treated.

8. The method of claim 7, wherein the human experiences neurological damage and the buntanetap or the pharmaceutically acceptable salt thereof is administered chronically to treat the neurological damage in the human.

9. The method of claim 1, wherein the buntanetap or the pharmaceutically acceptable salt thereof is administered (i) orally in an amount from about 1 mg to about 120 mg on a once-a-day basis; (ii) intravenously in an amount from about 0.1 mg to about 25 mg/day; or (iii) intraperitoneally/intramuscularly (IP/IM) in a dose from about 0.3 to about 70 mg/day.

10. The method of claim 1, wherein the buntanetap or the pharmaceutically acceptable salt thereof is administered orally in an amount from about 10 mg to about 80 mg on a once-a-day basis.

11. The method of claim 10, wherein peak plasma circulating levels of buntanetap in humans range from about 1 ng/ml to about 380 ng.

12. The method of claim 1, wherein the bacterium is *P. gingivalis*.

13. The method of claim 12, where *P. gingivalis* and its proteases infected astrocytes.

14. The method of claim 13, wherein the administering of the therapeutically effective amount of buntanetap of Formula (IV), (IV)

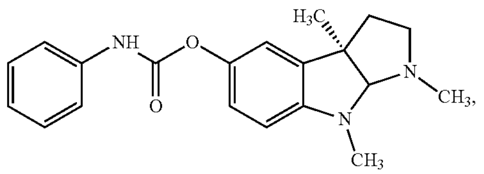

or a pharmaceutically acceptable salt thereof blocks gingipain-induced cell aggregation.

15. A method for prophylactically treating neurological damage from cytotoxicity to astrocytes in a healthy human who is at risk of exposure to infection by a bacterium that secretes gingipains, comprising administering to the human an effective amount of buntanetap of Formula (IV), (IV)

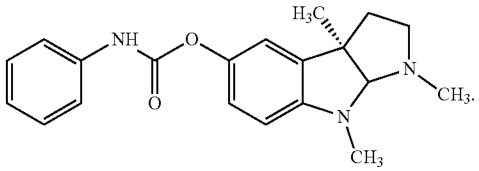

or a pharmaceutically acceptable salt thereof.

16. The method of claim 15, wherein the bacterium is *P. gingivalis*.

* * * * *